(12) United States Patent
Janik

(10) Patent No.: US 7,067,819 B2
(45) Date of Patent: Jun. 27, 2006

(54) SYSTEMS AND METHODS FOR MEASUREMENT OR ANALYSIS OF A SPECIMEN USING SEPARATED SPECTRAL PEAKS IN LIGHT

(75) Inventor: Gary Janik, Palo Alto, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 0 days.

(21) Appl. No.: 10/846,170

(22) Filed: May 14, 2004

(65) Prior Publication Data

US 2005/0253080 A1    Nov. 17, 2005

(51) Int. Cl.
*G01J 3/28* (2006.01)
*G01J 1/42* (2006.01)
*G01N 23/20* (2006.01)
*G01D 18/00* (2006.01)
*G12B 13/00* (2006.01)

(52) U.S. Cl. ............... 250/372; 250/252.1; 378/70; 356/326

(58) Field of Classification Search ............... 250/372; 378/70; 356/320
See application file for complete search history.

(56) References Cited

U.S. PATENT DOCUMENTS

| 4,905,170 | A |   | 2/1990  | Forouhi et al. |
| 4,999,014 | A |   | 3/1991  | Gold et al. |
| 5,166,752 | A |   | 11/1992 | Spanier et al. |
| 5,181,080 | A |   | 1/1993  | Fanton et al. |
| 5,486,701 | A |   | 1/1996  | Norton et al. |
| 5,489,980 | A | * | 2/1996  | Anthony ................ 356/308 |
| 5,608,526 | A |   | 3/1997  | Piwonka-Corle et al. |
| 5,747,813 | A |   | 5/1998  | Norton |
| 5,771,094 | A | * | 6/1998  | Carter et al. ................ 356/326 |
| 5,877,859 | A |   | 3/1999  | Aspnes et al. |
| 5,910,842 | A | * | 6/1999  | Piwonka-Corle et al. ... 356/369 |
| 5,953,446 | A |   | 9/1999  | Opsal et al. |

(Continued)

FOREIGN PATENT DOCUMENTS

WO    99/45340    9/1999

(Continued)

OTHER PUBLICATIONS

Gullikson, E. et al. "A Soft X-ray/EUV Reflectometer Based on a Laser Produced Plasma Source". Journal of X-ray Science and Technology 3, (1992), pp. 283-299.*

(Continued)

*Primary Examiner*—David Porta
*Assistant Examiner*—Frederick F. Rosenberger
(74) *Attorney, Agent, or Firm*—Ann Marie Mewherter; Daffer McDaniel, LLP

(57) ABSTRACT

A system configured for measurement of a specimen is provided. The system includes an optical subsystem configured to perform measurements of the specimen. The optical subsystem includes a light source that is configured to generate light having a relatively large number of separated spectral peaks with substantially no continuous background. In some embodiments, the light may include vacuum ultraviolet light, extreme ultraviolet light, and/or soft x-rays. A carrier medium is also provided that includes program instructions executable on a computer system to analyze data generated by a detector of an optical subsystem by partitioning the data into individual peaks spaced apart across a wavelength spectrum. Partitioning the data preferably corrects for spectrum shift, drift, stretching, shrinking, or a combination thereof at the detector. The individual peaks correspond to separated spectral peaks in light generated by a light source of the optical subsystem.

22 Claims, 9 Drawing Sheets

U.S. PATENT DOCUMENTS

| | | |
|---|---|---|
| 6,052,401 A | 4/2000 | Wieser et al. |
| 6,177,995 B1 | 1/2001 | Compain et al. |
| 6,181,421 B1 | 1/2001 | Aspnes et al. |
| 6,184,984 B1 | 2/2001 | Lee et al. |
| 6,211,957 B1 | 4/2001 | Erdogan et al. |
| 6,261,853 B1 | 7/2001 | Howell et al. |
| 6,269,144 B1 * | 7/2001 | Dube et al. ............ 378/71 |
| 6,282,222 B1 | 8/2001 | Wieser et al. |
| 6,325,078 B1 | 12/2001 | Kamieniecki |
| 6,400,089 B1 | 6/2002 | Salvermoser et al. |
| 6,440,760 B1 * | 8/2002 | Cho et al. ............ 438/16 |
| 6,456,362 B1 | 9/2002 | Banine |
| 6,515,746 B1 | 2/2003 | Opsal et al. |
| 6,519,045 B1 | 2/2003 | Kwon |
| 6,522,717 B1 | 2/2003 | Murakami et al. |
| 6,532,076 B1 | 3/2003 | Sidorowich |
| 6,535,286 B1 | 3/2003 | Green et al. |
| 6,555,485 B1 | 4/2003 | Liu et al. |
| 6,559,007 B1 | 5/2003 | Weimer |
| 6,583,876 B1 | 6/2003 | Opsal et al. |
| 6,591,024 B1 | 7/2003 | Westbrook |
| 6,610,614 B1 | 8/2003 | Niimi et al. |
| 6,610,615 B1 | 8/2003 | McFadden et al. |
| 6,611,330 B1 | 8/2003 | Lee et al. |
| 6,624,393 B1 | 9/2003 | Howell et al. |
| 6,633,831 B1 | 10/2003 | Nikoonahad et al. |
| 6,710,354 B1 | 3/2004 | Koch et al. |
| 2002/0018217 A1 | 2/2002 | Weber-Grabau et al. |
| 2003/0137662 A1 | 7/2003 | Janik et al. |
| 2004/0150820 A1 | 8/2004 | Nikoonahad et al. |

FOREIGN PATENT DOCUMENTS

| | | |
|---|---|---|
| WO | 00/65331 | 11/2000 |
| WO | 02/25723 | 3/2002 |

OTHER PUBLICATIONS

OBB Light Sources—Lamp Emission Spectra. Datasheet [online]. Photon Technology International, 2004 [retrieved on Jul. 14, 2005]. Retrieved from the Internet: <URL:http://www.pti-nj.com/obb_spectra.html>.*

Samson et al., *Vacuum Ultraviolet Spectroscopy I*, © 1998 by Academic Press, pp. 77.

International Search Report, PCT/US2005/016843, mailed Jan. 20, 2006.

* cited by examiner

SYSTEMS AND METHODS FOR MEASUREMENT OR ANALYSIS OF A SPECIMEN USING SEPARATED SPECTRAL PEAKS IN LIGHT

BACKGROUND OF THE INVENTION

1. Field of the Invention

The present invention generally relates to systems and methods for measurement or analysis of a specimen using separated spectral peaks in light. Certain embodiments relate to a system configured for measurement of a specimen that includes a light source configured to generate light having a relatively large number of separated spectral peaks with substantially no continuous background.

2. Description of the Related Art

Optical systems play a significant role in the manufacturing of integrated circuits and other semiconductor devices. For example, optical lithography tools are used to transfer a pattern from a reticle to a resist coated wafer. The patterned features on the wafer can then be used to form various features of integrated circuits and semiconductor devices. In addition, optical metrology and/or inspection tools are used for quality control purposes in semiconductor manufacturing. The capability and throughput of these optical systems can have a significant impact on semiconductor manufacturing. For example, the throughput of an optical lithography or metrology and/or inspection tool has a direct impact on the throughput of a semiconductor manufacturing process (e.g., as the throughput of the tool decreases, the throughput of the process decreases). In addition, the resolution of a lithography tool often determines the lateral dimensions of features of an integrated circuit. Therefore, the resolution of the lithography tool can determine other characteristics of the integrated circuit such as the performance bin characteristics. Likewise, the resolution capability of an optical metrology and/or inspection tool can have a significant impact on a semiconductor manufacturing process since the accuracy of the optical metrology and/or inspection tool can directly affect how well the process is controlled.

The resolution of an optical system depends to a large extent on the wavelength of the optical system as well as other parameters such as numerical aperture (NA). For example, as the wavelength of the optical system is decreased, the optical system can image features having smaller and smaller dimensions thereby increasing the resolution of the system. Decreasing the wavelength of a system such as a lithography tool is one way for semiconductor manufacturers to image features onto a wafer having smaller dimensions. Many lithography tools used in semiconductor manufacturing today are designed for use with light having a wavelength of 248 nm. However, lithography tools that are designed for use with light having a wavelength of 193 nm are becoming more prevalent in semiconductor research and manufacturing.

At wavelengths around 193 nm, light may be partially absorbed by water, oxygen, and air that is present in the optical path of an optical system. However, absorption levels at these wavelengths are not generally problematic. In contrast, as the wavelength of optical systems falls below 190 nm, absorption of the light by water, oxygen, and air can cause significant problems for these systems. For instance, in lithography tools designed for use at 157 nm, the amount of light available for imaging a resist on a wafer may be insufficient due to the absorption of the light by air in the lithography tool. Furthermore, many of the light sources that are able to produce light at wavelengths less than 190 nm are relatively low intensity or power light sources. Therefore, any absorption of the light by the environment in the lithography tool can result in a severe reduction in the imaging capability of the optical system.

To reduce the amount of light that is lost to absorption by air, some systems can be designed to generate a vacuum in which the optical components of the systems and the specimen that is being imaged can be placed. Since generating and maintaining a vacuum can be relatively expensive, however, more common methods for reducing absorption of light having wavelengths less than 190 nm involve purging the housing in which the optical components and the specimen are placed. Purging the housing or the tool generally involves replacing the ambient environment within the housing or tool with relatively pure gas such as nitrogen. There are, however, several problems with the current methods that are used to purge optical systems. For example, currently used methods of purging generally involve purging a relatively large region of the tool (e.g., the entire tool or the entire measurement chamber). In addition, purging a large region of the tool takes a significant amount of time. Therefore, purging can have a significant adverse impact on the throughput of the optical system.

Accordingly, it would be advantageous to develop systems and methods for optical tools that are designed to use light that is at least partially absorbed by air and that have more efficient purging systems than those described above.

SUMMARY OF THE INVENTION

An embodiment of the invention relates to a system for measurement of a specimen. The system includes a first optical subsystem configured to perform first measurements of the specimen. The first optical subsystem is disposed within a purged environment during the first measurements. The system also includes a second optical subsystem configured to perform second measurements of the specimen. The second optical subsystem is disposed within a non-purged environment during the second measurements.

In one embodiment, the first optical subsystem is configured to perform the first measurements using vacuum ultraviolet (VUV) light. In another embodiment, the second optical subsystem is configured to perform the second measurements using non-vacuum ultraviolet (non-VUV) light. In other embodiments, the first optical subsystem may be configured to perform the first measurements using VUV light and non-VUV light. In such an embodiment, the first optical subsystem may include one or more filters configured to prevent a substantial amount of the VUV light from reaching the specimen during measurements with the non-VUV light.

In some embodiments, if the first optical subsystem is configured to perform the first measurements using VUV light, the first measurements may include a thin film measurement. In one such embodiment, if the second optical subsystem is configured to perform the second measurements using non-VUV light, the second optical subsystem may be configured as a scatterometer. In additional embodiments, the first optical subsystem may be configured as a reflectometer, and the second optical subsystem may be configured as an ellipsometer. In an alternative embodiment, the first optical subsystem may be configured as an ellipsometer, and the second optical subsystem may be configured as a reflectometer.

In another embodiment, the first optical subsystem is configured as a spectroscopic ellipsometer or a spectroscopic reflectometer. In such an embodiment, the second optical subsystem may be configured as a single wavelength optical subsystem. In a different embodiment, the first optical subsystem may include an excimer light source configured to generate light having a wavelength of about 157 nm. According to one such embodiment, the first optical subsystem may be configured as a single wavelength ellipsometer. In another different embodiment, the first optical subsystem may be configured as a dual beam spectrophotometer. The first optical subsystem may also be configured such that both channels of the dual beam spectrophotometer are purged to substantially the same level during the first measurements.

In some embodiments, the first optical subsystem may include reflective focusing optics and reflective collecting optics. Alternatively, the first optical subsystem may include reflective focusing optics and transmissive collecting optics. In another alternative, the first optical subsystem may include transmissive focusing optics and reflective collecting optics. In additional embodiments, the first optical subsystem may include one or more hollow optical fibers. For example, the first optical subsystem may include a light source coupled to optical components by one or more hollow optical fibers. The system may be configured to move the optical components with respect to the specimen to perform the first measurements at different locations on the specimen. In such an embodiment, the light source may be substantially stationary during movement of the optical components.

In an additional embodiment, the system may include a differential purging subsystem configured to provide the purged environment for the first optical subsystem. In some embodiments, the specimen may be disposed within a different purged environment during the first measurements. In addition, the different purged environment may have a higher level of unwanted molecules than the purged environment. In a further embodiment, the system may include a specimen chamber. The specimen chamber may be configured to open to allow the specimen to be placed within the specimen chamber. The specimen chamber may also be configured to be purged after the specimen is placed within the specimen chamber and before the first measurements.

In another embodiment, the system may include a cleaning subsystem configured to remove contaminants from a portion of the specimen prior to the first measurements by the first optical subsystem. In some embodiments, the system may be configured to calibrate the first optical subsystem with data generated by the second optical subsystem. In addition, the system may be configured to use data generated by the first and second optical subsystems in combination to determine one or more properties of the specimen. The system may be further configured as described herein.

Another embodiment relates to a different system configured for measurement of a specimen. The system includes a first optical subsystem configured to perform first measurements of the specimen using VUV light. The system also includes a second optical subsystem configured to perform second measurements of the specimen using non-VUV light. In one embodiment, the second optical subsystem may be configured as a single wavelength ellipsometer. In a different embodiment, the second optical subsystem may be configured as a beam profile reflectometer. In another embodiment, the second optical subsystem may include a laser light source.

In one embodiment, the system may be configured to maintain a purged environment around the first optical subsystem during the first measurements. In some embodiments, the system may include a differential purge subsystem configured to maintain a purged environment around the first optical subsystem during the first measurements. In addition, the second optical subsystem may be disposed within a non-purged environment. The system is also configured to calibrate the first optical subsystem with data generated by the second optical subsystem. For example, the system may include a processor that is coupled to the first optical subsystem and the second optical subsystem. The processor may be configured to calibrate the first optical subsystem with the data generated by the second optical subsystem. The system may be further configured as described herein.

An additional embodiment relates to a computer-implemented method for analysis of a specimen. The method includes determining one or more properties of the specimen using first data in combination with second data. The first data is measured at a VUV wavelength, and the second data is measured at a non-VUV wavelength. The first data may be measured with a first optical subsystem, and the second data may be measured with a second optical subsystem. The first and second optical subsystems may be arranged within a single system. In addition, the first optical subsystem may be disposed within a purged environment in the system, and the second optical subsystem may be disposed within a non-purged environment.

The one or more properties that are determined may include optical properties of an upper layer on the specimen, optical properties of more than one layer on the specimen, critical dimension of a feature on the specimen, shape parameters of the feature on the specimen, overlay offset between two layers on the specimen, or a combination thereof. In one embodiment, the one or more properties may be determined using one or more algorithms. The one or more algorithms may include a genetic algorithm, a non-linear regression algorithm, or a comparison algorithm. In some embodiments, the first and second data may include scatterometry data. In such an embodiment, the one or more properties may be determined using one or more genetic algorithms.

According to an embodiment, the one or more properties may include optical properties of a structure on the specimen at the VUV wavelength. In such an embodiment, the second data may be used to determine a thickness of the structure on the specimen. The thickness may be used in combination with the first data to determine the optical properties. According to a different embodiment, the one or more properties may include an atomic concentration of one or more structures on the specimen. In one such embodiment, the atomic concentration may be determined from optical properties of the one or more structures. The optical properties may be determined from the first data, the second data, or the first and second data. In a different such embodiment, the atomic concentration may be determined by comparison of the first and second data with reference data. The computer-implemented method may include additional steps as described herein.

A further embodiment relates to another system for measurement of a specimen. The system includes a dual channel optical subsystem configured to perform measurements of the specimen using VUV light. In an embodiment, the dual channel optical subsystem may be configured as a dual beam spectrophotometer. This system also includes a purging subsystem configured to maintain a purged environment around the dual channel optical subsystem during the measurements. The purging subsystem is also configured to maintain the same level of purging in both channels of the dual channel optical subsystem. In one embodiment, the purging subsystem may include a differential purging subsystem.

In some embodiments, the system may include one or more additional optical subsystems configured to perform additional measurements of the specimen using non-VUV light. The one or more additional optical subsystems may be disposed within a non-purged environment. In a different embodiment, the system may include an additional optical subsystem disposed within the purged environment. The additional optical subsystem may be configured as a spectroscopic ellipsometer. The additional optical subsystem may include a VUV light flash lamp.

In another embodiment, the dual channel optical subsystem may be configured to perform additional measurements using non-VUV light. In one such embodiment, the dual channel optical subsystem may include one or more filters that are configured to prevent a substantial amount of the VUV light from reaching the specimen during the additional measurements with the non-VUV light.

In some embodiments, the dual channel optical subsystem may include reflective focusing optics and reflective collecting optics. Alternatively, the dual channel optical subsystem may include reflective focusing optics and transmissive collecting optics. In a different alternative, the dual channel optical subsystem may include transmissive focusing optics and reflective collecting optics. According to another embodiment, the dual channel optical subsystem may include one or more hollow optical fibers. In additional embodiments, the system may include a cleaning subsystem configured to remove contaminants from a portion of the specimen prior to the measurements. This system may be further configured as described herein.

Yet another embodiment relates to a different system configured for measurement of a specimen. The system includes two or more optical subsystems configured to perform measurements of the specimen using VUV light. The system also includes a purging subsystem configured to maintain a purged environment around the two or more optical subsystems during the measurements. The purging subsystem may be further configured to maintain approximately the same level of purging in the two or more optical subsystems. In one embodiment, the purging system is a differential purging subsystem.

In one embodiment, the two or more optical subsystems include a broadband reflective spectrometer and a broadband spectroscopic ellipsometer. The two or more optical subsystems may also be configured to perform additional measurements of the specimen using non-VUV light. In addition, the two or more optical subsystems may include one or more filters that are configured to prevent a substantial amount of the VUV light from reaching the specimen during the additional measurements with the non-VUV light. In another embodiment, the system also includes one or more additional optical subsystems configured to perform additional measurements of the specimen using non-VUV light. In one such embodiment, the one or more additional optical subsystems may include a beam profile ellipsometer, a beam profile reflectometer, a broadband reflective spectrometer, or a combination thereof. The one or more additional optical subsystems may be disposed within a non-purged environment.

In some embodiments, a first portion of the one or more additional optical subsystems may be disposed within the purged environment, and a second portion of the one or more additional optical subsystems may be disposed within a non-purged environment. In addition, the two or more optical subsystems and the one or more additional optical subsystems may have at least one common optical component, which may include the first portion of the one or more additional optical subsystems. The system may be further configured as described herein.

An additional embodiment relates to another system for measurement of a specimen. The system includes an optical subsystem configured to perform measurements of the specimen using VUV light and non-VUV light. In one embodiment, the optical subsystem includes one or more filters that are configured to prevent a substantial amount of the VUV light from reaching the specimen during the measurements with the non-VUV light. The system also includes a purging subsystem configured to maintain a purged environment around the optical subsystem during the measurements. The purging subsystem may be a differential purging subsystem.

In an embodiment, the optical subsystem may be configured as a spectroscopic ellipsometer or a spectroscopic reflectometer. In such an embodiment, the optical subsystem may also be configured as a single wavelength ellipsometer. In another embodiment, the optical subsystem may be configured to perform thin film measurements using the VUV light. The optical subsystem may also be configured to perform scatterometry measurements using the non-VUV light. In an additional embodiment, if the optical subsystem is configured as a single wavelength ellipsometer, the single wavelength ellipsometer may include an excimer light source that is configured to generate light having a wavelength of about 157 nm. In a different embodiment, if the optical subsystem may be configured as a spectroscopic ellipsometer, the spectroscopic ellipsometer may include a flash lamp configured to generate the VUV light.

The optical subsystem may include one or more hollow optical fibers. In some embodiments, the optical subsystem may include a light source that is coupled to optical components by one or more hollow optical fibers. The system may be configured to move the optical components with respect to the specimen to perform the measurements at different locations on the specimen. The light source may be substantially stationary during movement of the optical components. In one embodiment, the optical subsystem may include reflective focusing optics and reflective collecting optics. Alternatively, the optical subsystem may include reflective focusing optics and transmissive collecting optics. In another alternative, the optical subsystem may include transmissive focusing optics and reflective collecting optics.

In another embodiment, the specimen may be disposed within a different purged environment during the measurements. In one such embodiment, the different purged environment may have a higher level of unwanted molecules than the purged environment. In some embodiments, the system may include a specimen chamber that is configured to open to allow the specimen to be placed within the specimen chamber. The specimen chamber may also be configured to be purged after the specimen is placed within the specimen chamber and before the measurements. The system may be further configured as described herein.

Further embodiments relate to another system for measurement of a specimen. The system includes a cleaning subsystem that is configured to remove contaminants from the specimen prior to measurement. In one embodiment, the cleaning subsystem may include a laser-based cleaning subsystem. The cleaning subsystem may be configured to remove contaminants from a localized area on the specimen. In a different embodiment, the cleaning subsystem may be a heat-based cleaning subsystem. Such a cleaning subsystem may be configured to remove contaminants from substantially an entire surface of the specimen.

The system also includes an optical subsystem that is configured to perform measurements of the specimen using VUV light. The optical subsystem is disposed within a purged environment. In some embodiments, the system may include a differential purging subsystem that is configured to provide the purged environment for the optical subsystem. However, the cleaning subsystem may be disposed within a non-purged environment.

In additional embodiments, the optical subsystem may also be configured to perform the measurements of the specimen using non-VUV light. In one such embodiment, the optical subsystem may include one or more filters that are configured to prevent a substantial amount of the VUV light from reaching the specimen during the measurements with the non-VUV light.

In one embodiment, the system may include an additional optical subsystem configured to perform additional measurements of the specimen using non-VUV light. The additional optical subsystem may be disposed within a non-purged environment. In a different embodiment, the system may include an additional optical subsystem that is configured to perform additional measurements of the specimen using YUV light. The additional optical subsystem may be disposed within the purged environment. The system may be further configured as described herein.

Some embodiments relate to another system configured for measurement of a specimen. This system includes an optical subsystem configured to perform measurements of the specimen. The optical subsystem includes a light source configured to generate light having a relatively large number of separated spectral peaks with substantially no continuous background. In one embodiment, the light may have wavelengths of less than about 200 nm. For example, the light may include VUV light. Alternatively, the light may include extreme ultraviolet (EUV) light. In another embodiment, the light may include soft x-rays. The relatively large number of separated spectral peaks may include about 10 or more separated spectral peaks.

In some embodiments, the optical subsystem may be configured as a spectroscopic ellipsometer, a polarimeter, a reflectometer, any other optical measurement subsystem known in the art, or a combination thereof. In such embodiments, the measurements may include measurements of thin film properties. In addition, the optical subsystem may include an array detector configured to detect light returned from the specimen. The optical subsystem may be further configured as described herein.

In one embodiment, the system may also include a processor coupled to the optical subsystem. In one such embodiment, the processor may be configured to process data generated by the optical subsystem by considering a signal from a peak in light detected by the optical subsystem as having a single wavelength. The single wavelength includes a known wavelength of a center of the peak. In another such embodiment, the processor may be configured to process data generated by the optical subsystem by summing signals for a peak in light detected by the optical subsystem if the peak spans more than one pixel on a detector of the optical subsystem. In an additional embodiment, the processor may be configured to process data generated by the optical subsystem by partitioning the data into individual peaks spaced apart across a wavelength spectrum. The individual peaks correspond to the separated spectral peaks of the light generated by the light source. These embodiments of a system configured for measurement of a specimen may be further configured as described herein.

Other embodiments relate to a carrier medium that includes program instructions. The program instructions are executable on a computer system to analyze data generated by a detector of an optical subsystem by partitioning the data into individual peaks spaced apart across a wavelength spectrum. The individual peaks correspond to separated spectral peaks in light generated by a light source of the optical subsystem. In one embodiment, the light generated by the light source may include a relatively large number of the separated spectral peaks with substantially no continuous background. The optical subsystem is configured to perform measurements of a specimen. In another embodiment, the optical subsystem may be configured as a spectroscopic ellipsometer, a polarimeter, a reflectometer, any other optical measurement subsystem known in the art, or a combination thereof. The optical subsystem may be further configured as described herein. In some such embodiments, the measurements may include measurements of thin film properties.

Partitioning of the data may maintain a wavelength calibration of the detector. Partitioning of the data may also increase an accuracy of the measurements of the optical subsystem that are performed as a function of wavelength. In addition, partitioning of the data may correct for spectrum shift, drift, stretching, shrinking, or a combination thereof at the detector.

In some embodiments, the program instructions may be further executable on the computer system to analyze the data by summing signals for one or more of the individual peaks if the one or more of the individual peaks span more than one pixel on the detector. In a different embodiment, the program instructions may be executable on the computer system to analyze the data by considering a signal from one or more of the individual peaks as having a single wavelength. The single wavelength includes a known wavelength of a center of the one or more of the individual peaks.

The light generated by the light source may have wavelengths of less than about 200 nm. For example, the light generated by the light source may include VUV light. In another example, the light generated by the light source may include EUV light. In a further example, the light generated by the light source may include soft x-rays. The embodiments of the carrier medium described above may be further configured as described herein. For example, the carrier medium may include additional program instructions executable on the computer system to perform additional computer-implemented methods described herein.

Additional embodiments relate to a method for measurement of a specimen. The method includes measuring spectroscopic ellipsometric data of the specimen. In one embodiment, the spectroscopic ellipsometric data may be measured at wavelengths from about 220 nm to about 900 nm. In a different embodiment, the spectroscopic ellipsometric data may be measured at wavelengths from about 190 nm to about 300 nm. In another different embodiment, the spectroscopic ellipsometric data may be measured at VUV wavelengths.

The method also includes determining a nitrogen concentration of a nitrided oxide gate dielectric formed on the specimen from the spectroscopic ellipsometric data. In one embodiment, the spectroscopic ellipsometric data may be measured at multiple locations on the specimen. In one such embodiment, the method may include determining the nitrogen concentration at the multiple locations and determining a within wafer (WIW) uniformity of the nitrogen concentration. In another embodiment, the method includes determining a thickness and an index of refraction of the nitrided oxide gate dielectric using the spectroscopic ellipsometric data. In some embodiments, the method may include determining an index of refraction of the nitrided oxide gate dielectric from the spectroscopic ellipsometric data and determining the nitrogen concentration from the index of refraction.

In an additional embodiment, the method may also include measuring reflectometric data of the specimen. In such an embodiment, determining the nitrogen concentration may include determining the nitrogen concentration from the spectroscopic ellipsometric data in combination with the reflectometric data. The spectroscopic ellipsometric data and the reflectometric data may be measured with one system. In some embodiments, the method may include removing contaminants from a localized area on the specimen using a laser-based cleaning subsystem prior to measurement of the spectroscopic ellipsometric data. The spectroscopic ellipsometric data may be measured at the localized area.

In one embodiment, measuring the spectroscopic ellipsometric data may be performed during a semiconductor fabrication process. In another embodiment, the method may include altering one or more parameters of a semiconductor fabrication process based on the nitrogen concentration. In an additional embodiment, the method may include monitoring one or more parameters of a semiconductor fabrication process using the nitrogen concentration. The method may include any additional steps of any methods described herein.

Other embodiments relate to a computer-implemented method for analysis of a specimen. The computer-implemented method includes determining a nitrogen concentration of a nitrided oxide gate dielectric formed on the specimen from spectroscopic ellipsometric data generated by measurement of the specimen. In one embodiment, the spectroscopic ellipsometric data may be measured at wavelengths from about 220 nm to about 900 nm. Alternatively, the spectroscopic ellipsometric data may be measured at wavelengths from about 190 nm to about 300 nm. In another alternative, the spectroscopic ellipsometric data may be measured at VUV wavelengths. In some embodiments, the spectroscopic ellipsometric data may be measured at multiple locations on the specimen. In such embodiments, the method may also include determining the nitrogen concentration at the multiple locations and determining a WIW uniformity of the nitrogen concentration.

In one embodiment, the method may include determining a thickness and an index of refraction of the nitrided oxide gate dielectric using the spectroscopic ellipsometric data. In another embodiment, the method may include determining an index of refraction of the nitrided oxide gate dielectric from the spectroscopic ellipsometric data and determining the nitrogen concentration from the index of refraction. In other embodiments, determining the nitrogen concentration may include determining the nitrogen concentration from the spectroscopic ellipsometric data in combination with reflectometric data generated by measurement of the specimen.

Additional embodiments of the method may include determining one or more parameters of a semiconductor fabrication process based on the nitrogen concentration. In one embodiment, the method may also include monitoring one or more parameters of a semiconductor fabrication process using the nitrogen concentration. The computer-implemented method may also include any other steps of any method described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
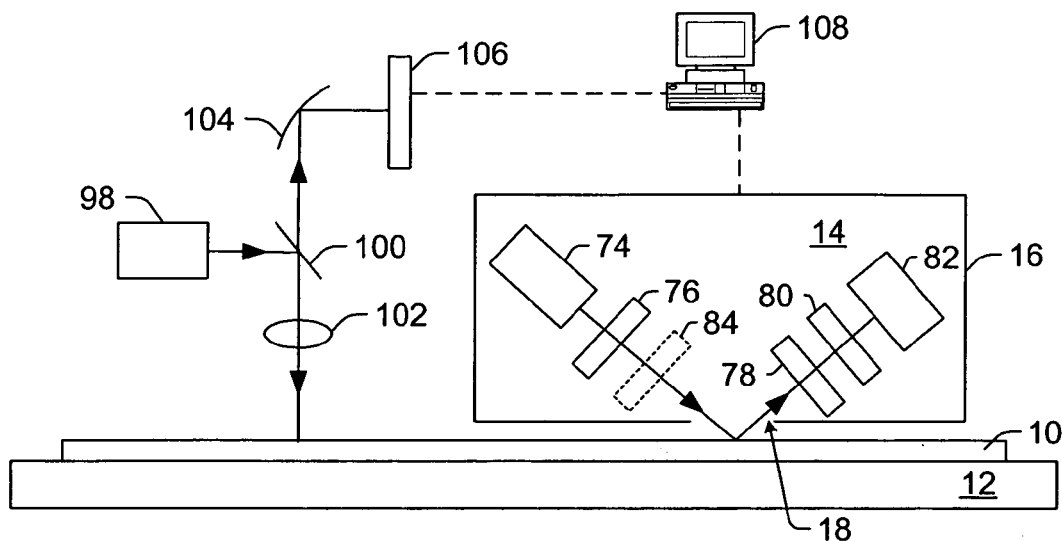
FIG. 1 is a schematic diagram illustrating a cross-sectional side view of one embodiment of a system configured for measurement of a specimen.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The following description generally relates to optical systems configured to operate at wavelengths which advantageously use a purged environment. By purging only those optical subsystems that actually benefit from purging, cost can be saved, and reliability can be improved. The embodiments described herein could be very important to economically manufacturing systems that operate at relatively low wavelengths (e.g., vacuum ultraviolet or near vacuum ultraviolet wavelengths). For example, the alternative is to enclose the whole system in a chamber filled with an inert gas (or vacuum) with a load lock to allow loading and unloading of specimens without introducing too much oxygen, water, carbon dioxide, etc. Such an approach results in slower wafer transfer, more restricted access to the optics for alignment, and makes the system more expensive.

As used herein, the term "specimen" generally refers to a wafer or a reticle. As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include only the substrate such as a virgin wafer. Alternatively, a wafer may include one or more layers formed upon a substrate. For example, such layers may include, but are not limited to, a resist, a dielectric material, and a conductive material. A resist may include any material that may be patterned by an optical lithography technique, an e-beam lithography technique, or an X-ray lithography technique. Examples of a dielectric material may include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials such as "xero-gels," and "high-k" dielectric materials such as tantalum pentoxide. In addition, examples of a conductive material include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used interchangeably herein with the term "integrated circuit."

The specimen may further include at least a portion of a thin-film head die formed on a wafer, at least a portion of a micro-electro-mechanical system (MEMS) device formed on a wafer, flat panel displays, magnetic heads, magnetic and optical storage media, and at least a portion of other components that may include photonics and optoelectronic devices such as lasers, waveguides and other passive components processed on wafers, print heads, and bio-chip devices processed on wafers.

A "reticle," or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source.

As used herein, the term "lithography system" generally refers to any lithography system that prints images of a reticle onto a wafer using light. The lithography system may be a scanning projection system or a step and scan system, which are both commonly referred to as a "scanner" or a step-and-repeat system, also called a "stepper." The lithography system may include any exposure system known in the art such as systems commercially available from Nikon, ASM Lithography, Canon, or Integrated Solutions, Inc. The terms "lithography system," "scanner," and "stepper" are used interchangeably herein.

As used herein, the term "vacuum ultraviolet light" or "VUV light" refers to ultraviolet light that will be significantly absorbed by air, oxygen, carbon dioxide, and water molecules. VUV light generally includes light having a wavelength of less than about 190 nm. The term "non-vacuum ultraviolet light" or "non-VUV light" refers to deep ultraviolet light, ultraviolet light, visible light, infrared light, or any combination thereof. Generally, the term non-VUV light refers to any light having a wavelength greater that about 190 nm. In addition, the term "near vacuum ultraviolet light" or "near VUV light" is used to refer to light having a wavelength of about 193 nm (e.g., about 190 nm to about 200 nm), which is partially transmissive in the atmosphere. VUV light, non-VUV light, and near VUV light may be monochromatic, near monochromatic, polychromatic, or broadband light.

As used herein, the term "measurement" refers to any measurements that may be performed on a wafer, reticle, or other specimen. For example, measurements may include thin film measurements, measurement of a lateral dimension of a layer or feature on the wafer, detection of defects on the wafer (i.e., inspection), and determination of one or more properties of the defects on the wafer. In addition, the measurements may include any other measurements of a wafer, reticle, or other specimen known in the art.

As used herein, the term "reference data" refers to data measured on a reference specimen that includes one or more layers having a known atomic concentration.

As used herein, the term "structure" refers to a layer, interface, feature, or region of a specimen.

The terms "first" and "second" as used herein are not to be construed as sequential or temporal indicators. Instead, the terms first and second are used to identify different subsystems, measurements, data, etc.

Turning now to the drawings, it is noted that FIGS. 1–18 are not drawn to scale. In particular, the scale of some of the elements of the figures are greatly exaggerated to emphasize characteristics of the elements. It is also noted that FIGS. 1–18 are not drawn to the same scale. Elements shown in more than one figure that may be similarly configured have been indicated using the same reference numerals.

FIG. 1 illustrates one embodiment of a system configured for measurement of specimen 10. The system includes stage 12 upon which specimen 10 is disposed during measurement. Stage 12 may be a vacuum chuck, an electrostatic chuck, or any other device configured to hold the specimen in place during measurement. The stage may be coupled to a mechanical assembly (not shown). The mechanical assembly may be configured to move the stage and thereby the specimen such that measurements can be performed in different locations on the specimen. The mechanical assembly may be configured to rotate the specimen during measurement. The mechanical assembly may also be configured to translate the specimen laterally. The mechanical assembly may be configured to rotate and translate the specimen at the same time such that the light beam is scanned over the specimen in a spiral-like path. A stage coupled to such a mechanical assembly may be commonly referred to as an "rθ stage." In some embodiments, the speeds at which the specimen is rotated and translated may be varied during scanning to maintain a substantially constant scanning speed. In other embodiments, the mechanical assembly may be configured to translate the specimen in two lateral directions, X and Y. A stage coupled to such a mechanical assembly may be commonly referred to as an "xy stage." In such embodiments, the mechanical assembly may be configured to translate the specimen such that the light beam is scanned over the specimen in a serpentine-like path. The mechanical assembly may include any suitable mechanical or robotic assembly known in the art. In some embodiments, the stage may include an edge handling mechanism. For example, the stage may include mechanical features (not shown) that are configured to contact the edge of the specimen and to support the specimen a spaced distance above the upper surface of the stage. In this manner, cross-contamination of the backside of the specimens may be reduced, and even prevented.

The system includes a first optical subsystem that is configured to perform first measurements of specimen 10. The first optical subsystem is disposed within purged environment 14 during the first measurements. In one embodiment, the first optical subsystem may be disposed in housing 16. The housing may include any suitable housing known in the art, and many different types are commercially available. Preferably, the housing may be selected or formed to have the smallest internal area while allowing sufficient space for the first optical subsystem. In this manner, the amount of time it takes to purge the housing may be kept to a minimum. In addition, the area within the system, but outside of housing 16 is a non-purged environment. Therefore, the amount of time that would otherwise be required to purged the entire measurement chamber or overall housing of the system is eliminated. Although housing 16 is shown in FIG. 1 to have a generally rectangular shape, it is to be understood that the housing may have any shape such as a cylindrical or an irregular shape.

As shown in FIG. 1, the housing includes an opening or aperture 18 (referred to herein as a "differential aperture") to allow the light from the first optical subsystem to impinge upon the specimen and to allow the light returned from the specimen to be collected or detected by the first optical subsystem. Such a differential aperture may be included in the housing if the light of the first optical subsystem will be absorbed by materials of the housing. Alternatively, the housing may be fitted with relatively small sections of a material that will not strongly absorb or otherwise alter the light of the first optical subsystem. However, since such materials can be relatively expensive (particularly for the wavelength(s) of the first optical subsystem described below), it may be preferable to provide a differential aperture in the housing. The differential aperture may have any shape, but its dimensions are preferably kept as small as possible thereby reducing the amount of ambient molecules or gases that migrate into the housing through the differential aperture. In addition, other measures may be taken to reduce the amount of ambient molecules or gases that flow through the differential aperture. For example, the distance between the lower surface of the housing and the specimen may be reduced or minimized.

A purging subsystem (not shown in FIG. 1) may be coupled to the housing. The purging subsystem may be configured to flow dry nitrogen ($N_2$) or another suitable dry inert gas into the housing such that the dry gas replaces the ambient gas in the housing. The purging subsystem may also be configured to flow sufficient dry $N_2$ into the housing at a flow rate that reduces the amount of ambient molecules or gases that flow through the differential aperture. In addition, the purging subsystem may be configured to purge the housing with a substantially clean gas. For example, the purging subsystem may include a filtration system configured to filter contaminants from the dry inert gas before it is introduced into the housing. Such filtration systems are known in the art.

Housing 16 may be purged prior to measurements by the first optical subsystem while at times during which no measurements are to be performed, the environment within the housing may be non-purged or ambient. Alternatively, housing 16 may be continually purged by the purged subsystem, which may be suitable for applications such as manufacturing where the time in which the housing is purged may reduce the throughput of the manufacturing process.

Preferably, the purging subsystem is configured to provide a purged environment for the first optical subsystem that is substantially free of water, air, oxygen, carbon dioxide, and other absorbing molecules (collectively referred to herein as "unwanted molecules"). Such purging subsystems are generally known in the art, and although one particularly suitable purging subsystem will be described further below, it is to be understood that the purging subsystem may include any suitable commercially available purging subsystem. The purging subsystem preferably removes the unwanted molecules from the environment in which the first optical subsystem is disposed because at least some of the wavelengths at which the first optical subsystem operates would otherwise be substantially absorbed by these unwanted molecules. For example, the first optical subsystem may be configured to perform the first measurements of the specimen using at least some wavelengths of VUV light. In particular, the first optical subsystem may be configured to perform the first measurements of the specimen using VUV light or VUV light in addition to non-VUV light.

In addition, as described above, the distance between the housing and the specimen may be reduced or kept at a minimum to reduce the amount of unwanted molecules that flow into the housing through the differential aperture. However, keeping the distance between the housing and the specimen at a minimum also reduces the distance that the light of the first optical subsystem travels outside of the housing. Therefore, keeping this distance at a minimum will minimize the amount of absorption that light of the first optical subsystem experiences outside of the housing due to the ambient environment. Other elements shown in FIG. 1 are described in further detail below.

Figure 2:
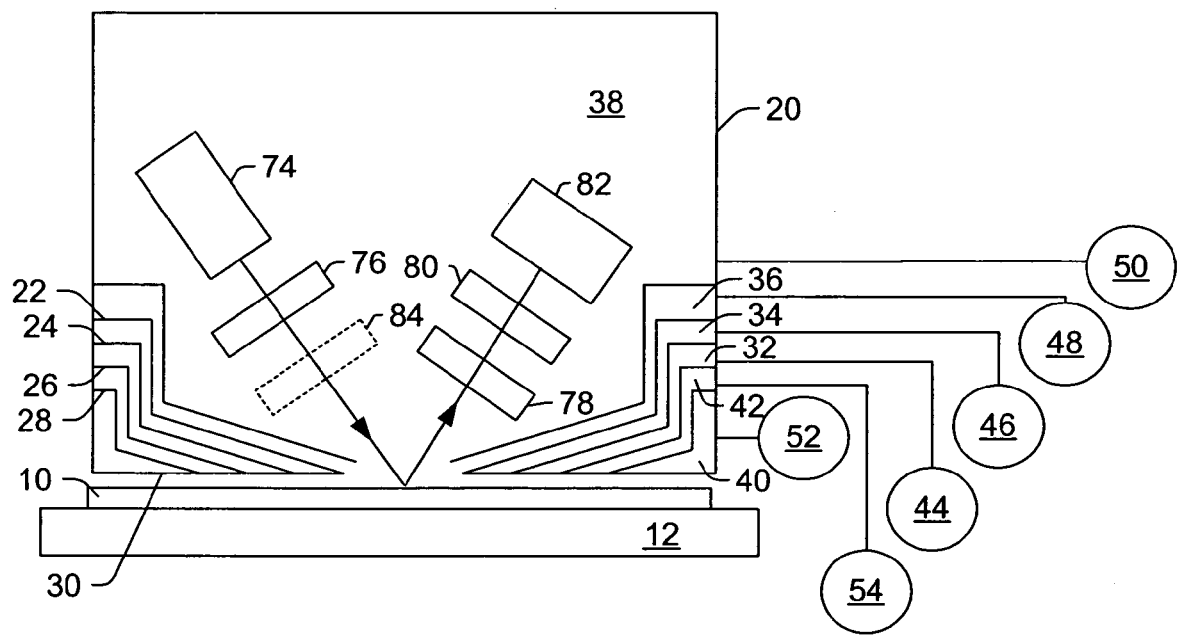
FIG. 2 is a schematic diagram illustrating a cross-sectional side view of one embodiment of a differential purging subsystem configured to provide a purged environment for an optical subsystem.

FIG. 2 illustrates one embodiment of a purging subsystem that may be used to provide the purged environment for the first optical subsystem. This purging subsystem is similar to the multiple stage, non-contact vacuum seal described in U.S. patent application Ser. No. 10/052,307 entitled "Scanning Electron Microscope Architecture and Related Material Handling System" filed on Jan. 17, 2002, by Koch et al., which is incorporated by reference as if fully set forth herein. However, in the embodiment shown in FIG. 2, multiple stage, non-contact seal 20 is used to provide a purged, non-vacuum environment. In this embodiment, seal 20 includes four concentric metal rings 22, 24, 26, and 28. In this embodiment, the rings are fabricated from anodized aluminum ($Al_2O_3$), although other materials such as titanium could be used. Proper attachment of these rings to the housing ensures that their lower surfaces 30 are coplanar within approximately one micron.

Purging stage 20 has four purging stages. Stage 32, the outer stage, is purged with dry $N_2$ or another dry gas but contains the highest levels of unwanted molecules of the four purging stages. Stage 34 is purged to have levels of unwanted molecules that are lower than those contained in stage 32. Likewise, stage 36 is purged to have levels of unwanted molecules that are lower than those contained in stage 34. Stage 38, the fourth and innermost stage, is purged to a level such that this stage is substantially free of unwanted molecules. Stages 32, 34, 36, and 38 may be individually coupled to separate assemblies 44, 46, 48, and 50, respectively. The assemblies may include pumps, tubing, filter, and other hardware suitable to independently provide the purged environments within each of the stages. The assemblies can have any configuration known in the art, and such hardware is commercially available for these applications.

Overpressure vent 40 creates a ring of high pressure dry gas around the entire set of seals. The overpressure prevents moisture from migrating into the inner purging zones. Ambient pressure vent 42 creates a ring of ambient air pressure between the overpressure created by vent 40 and first purging stage 32. The ambient pressure zone prevents the high pressure gas discharged from vent 40 from migrating further inward towards the purging zones. Overpressure vent 40 and ambient pressure vent 42 may be individually coupled to separate assemblies 52 and 54, respectively. These assemblies may be configured as described above.

Although four purging stages are used in this embodiment, nothing herein should be taken to restrict the present invention to only using four stages. Fewer stages could be used if a greater pressure differential between each stage is acceptable although larger pumps might be required for each stage. Similarly, more stages could be used, but with an associated disadvantage of increased mechanical complexity, as well as increased weight. The shape of the seals is also not definitive of this embodiment. Although circular seals are easier to fabricate than some other shapes and match the shape of specimens such as semiconductor wafers, nothing herein requires that the seals be circular. Square, rectangular, or even irregularly shaped seals could be used without departing from the teachings of the present invention. The seals may also be used to match the shape of the housing and/or the optical subsystem contained within the purged environment. Multiple stage, non-contact seal 20 may be further configured as described in U.S. patent application Ser. No. 10/052,307.

Another example of a suitable purging subsystem is illustrated in U.S. patent application Ser. No. 10/718,126 entitled "Optical System for Measuring Samples Using Short Wavelength Radiation" filed Nov. 19, 2003 by Nikoonahad et al., which is incorporated by reference as if fully set forth herein. In this patent application, a method and apparatus are disclosed in which a differential seal (somewhat analogous to the seal described above, but preferably using a purge instead of vacuum) is maintained around the optical subsystem. The purged environment is used to prevent contamination of the optics and/or to avoid problems associated with dissociation of oxygen containing species due to exposure by short wavelength sources. The systems described herein are different from the apparatuses described by Nikoonahad et al., in that the purging subsystem is used to provide a purged environment for only some of the optical subsystems in a tool.

Figure 3:
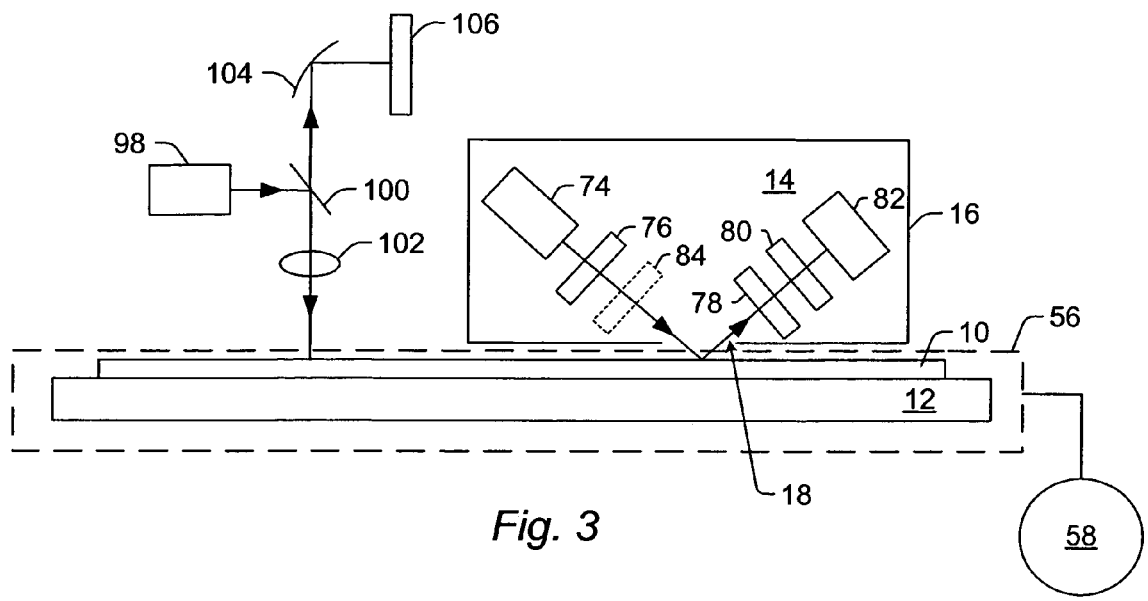
FIG. 3 is a schematic diagram illustrating a cross-sectional side view of one embodiment of a system configured for measurement of a specimen, in which the specimen is disposed within a purged environment during the measurements.

In another embodiment, the optics of the first optical subsystem is disposed in a purged environment with substantially low levels of unwanted molecules, with only one or a few differential apertures between the optics environment and the specimen environment, while the specimen environment is also enclosed but has higher levels of unwanted molecules than around the optics, and substantially lower levels of such molecules than the atmosphere. For example, the specimen may also be disposed within a purged environment during first measurements by the first optical subsystem. The purged environment in which the specimen is disposed may be different than the purged environment in which the first optical subsystem is disposed. For example, as shown in FIG. 3, the specimen may be disposed within purged environment 56. Purged environment 56 may be provided by a purging subsystem that includes assembly 58. The assembly may be configured as described above.

In some embodiments, unlike the first optical subsystem, the specimen may not be disposed within a housing. Instead, a dry $N_2$ or other dry inert gas may be flowed across the specimen, particularly in the area between the specimen and the first optical subsystem. Such a configuration may be suitable since the purged environment in which the specimen is disposed may have a higher level of unwanted molecules than the purged environment of the first optical subsystem. Such relaxed environmental conditions for the purged environment of the specimen may be sufficient since the distance between the first optical subsystem and the specimen is relatively short thereby providing less opportunity for the light of the first optical subsystem to be absorbed.

Figure 4:
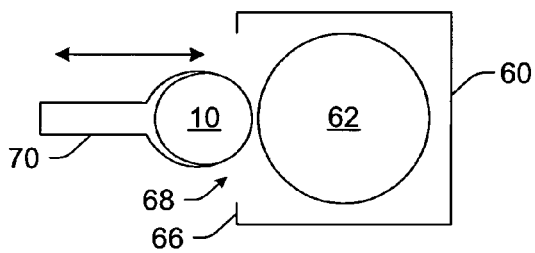
FIG. 4 is a schematic diagram illustrating a cross-sectional top view of one embodiment of a specimen chamber.
Figure 5:
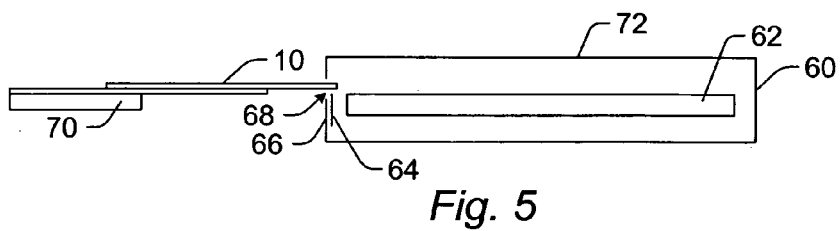
FIG. 5 is a schematic diagram illustrating a cross-sectional side view of the specimen chamber of FIG. 4.

In another embodiment, the system may include a specimen chamber in which the specimen may be disposed during measurement. One embodiment of a specimen chamber is illustrated in FIGS. 4 and 5. As shown in the cross-sectional top view of FIG. 4, the specimen chamber may include housing 60. Stage 62 is disposed within housing 60. The stage may be configured as described above. The specimen chamber is configured to open to allow a specimen to be placed within the specimen chamber. For example, as shown in the cross-sectional side view of FIG. 5, housing 60 may include door 64 coupled to side 66 of the housing. Door 64 may be lowered (or otherwise moved) away from opening 68 in side 66 of housing 60. Specimen 10 may then be moved through opening 68 by specimen handler 70. The specimen handler may include any suitable specimen handler known in the art such as a robotic wafer handler or other mechanical or motorized assembly. The specimen handler may place the specimen onto stage 62. The specimen handler may then be moved out of the housing, and the door of the housing may be moved over the opening to thereby enclose the specimen with housing. The specimen chamber may then be purged before the first measurements by the first optical subsystem. Therefore, a simple door may separate the specimen environment from the ambient environment allowing significant amounts of air to enter the housing when the specimen is loaded, which may be quickly purged to remove unwanted molecules to relatively low levels once the door is closed. Such an embodiment avoids the cost, space, and complexity of a full load lock but still keeps relatively low levels of unwanted molecules around the specimen and still lower levels of unwanted molecules around the optics.

The specimen chamber may be configured in a number of ways such that measurements of the specimen may be performed while the specimen is disposed within the specimen chamber. In one embodiment, upper surface 72 of the specimen chamber shown in FIG. 5 may be formed of a material that is optically transparent to light from the first optical subsystem as well as any other optical subsystems of the system. Since such materials may be relatively expensive for at least some of the wavelengths (e.g., the VUV wavelengths), in another embodiment, an opening or differential aperture (not shown) may be formed in upper surface 72 through which light from the first optical subsystem as well as any other optical subsystems of the system may pass. In some such embodiments, the differential aperture may have lateral dimensions that are approximately the same as the specimen. Alternatively, the differential aperture may have lateral dimensions that are much smaller than the lateral dimensions of the specimen, but are sufficient to allow light from at least the first optical subsystem to pass through the opening. In such an embodiment, the differential aperture may be moved in conjunction with scanning of the specimen by the first optical subsystem. For example, the differential aperture may be formed in a plate or relatively flat sheet of material that is moved in accordance with scanning by the first optical subsystem. However, since the amount of unwanted molecules in the purged environment around the specimen may be relatively high, and since having a differential aperture in the upper surface of the housing that has approximately the same lateral dimensions as the specimen would allow for a simpler configuration, such a configuration for the housing may be preferable.

Turning back to FIG. 1, FIG. 1 illustrates one embodiment of the first optical subsystem. In this embodiment, the first optical subsystem is configured as an ellipsometer. The ellipsometer includes light source 74. A variety of different light sources can be used to generate VUV wavelengths for the first optical subsystem. In one preferred embodiment, a deuterium ($D_2$) lamp is used. Typically, the lamp will have a window made of a material such as magnesium fluoride ($MgF_2$) that transmits well as such wavelengths. Excimer or high-intensity gas discharge lamps (such as those described in U.S. Pat. No. 6,052,401 to Wieser et al., U.S. Pat. No. 6,282,222 to Wieser et al., and U.S. Pat. No. 6,400,089 to Salvermoser et al., which are incorporated by reference as if fully set forth herein) could be used as narrow band light sources for use in an ellipsometer or reflectometer configuration including a multi-angle ellipsometer or a beam profile reflectometer. A flash lamp (filled with Xenon or other gas) or a Xenon arc lamp can also generate light at VUV wavelengths.

Light source 74 may be a monochromatic or near monochromatic light source. For example, the first optical subsystem may include an excimer light source configured to generate light having a wavelength of about 157 nm or another VUV wavelength. In such an embodiment, the ellipsometer may function as a single wavelength ellipsometer. Alternatively, light source 74 may be a polychromatic or broadband light source. For example, the first optical subsystem may include a flash lamp configured to generate light having VUV wavelengths. In this embodiment, the ellipsometer may function as a spectroscopic ellipsometer.

Light from light source 74 is directed to polarizer 76. In one embodiment, the polarizer may be a Rochon prism. In some embodiments, the polarizer may rotate such that the ellipsometer is configured as a rotating polarizer ellipsometer (RPE). Light passing through the polarizer is directed onto specimen 10.

Light reflected from the specimen is collected by analyzer 78. Analyzer 78 may include any polarizing element known in the art. In a RPE configuration, the position of the analyzer is fixed. However, in some embodiments, both polarizer 76 and analyzer 78 may rotate. One example of an ellipsometer system that includes a rotating polarizer and a rotating analyzer is disclosed in International Publication No. WO 00/65331 by Wang et al., which is incorporated by reference as if fully set forth herein. In a spectroscopic ellipsometer configuration, the first optical subsystem may include spectrometer 80 and detector 82. The spectrometer or another dispersion element may be configured to separate beam components having different wavelengths. The separated components of the beam may be detected by individual elements of an array of the detector. In a non-spectroscopic ellipsometer configuration, the first optical subsystem may include detector 82, but not spectrometer 80. Detector 82 may include any appropriate detector known in the art.

Although detector 82 is shown to be located within the purged environment contained within housing 16, it is to be understood that the detector and any associated electronics may alternatively be located outside of housing 16 and therefore outside of the purged environment for the first optical subsystem. In such an embodiment, a second differential aperture (not shown) may be formed within the housing. Light from the spectrometer may be directed through the additional differential aperture to the photosensitive elements of the detector. Placing the detector and any associated electronics outside of the purged environment within housing 16 may allow the area within the housing to be reduced thereby reducing the time it takes to create the purged environment and the cost of creating and maintaining the purged environment.

Although one particular ellipsometer configuration is shown in FIG. 1, it is to be understood that the ellipsometer may have any configuration known in the art. For example, the first optical subsystem may be configured as a rotating compensator ellipsometer (RCE), which is known in the art, or a beam profile ellipsometer, which is described further herein. In addition, the ellipsometer may be configured as a variable angle ellipsometer. Further examples of ellipsometer configurations are illustrated in U.S. patent application Ser. No. 10/056,271 entitled "Laser-Based Cleaning Device For Film Analysis Tool," by Janik et al. and U.S. Pat. No. 5,166,752 to Spanier et al., U.S. Pat. No. 5,608,526 to Piwonka-Corle et al., U.S. Pat. No. 5,910,842 to Piwonka-Corle et al., and U.S. Pat. No. 6,515,746 to Opsal et al., all of which are incorporated by reference as if fully set forth herein. Such systems, if configured for use at VUV wavelengths, can also benefit from the purging configurations described herein.

In one embodiment, the purged environment around the optics and the differential aperture may be used to improve the signal level for measurements made at wavelengths that are partially transmissive in the atmosphere (and thus cannot be strictly called VUV) such as 193 nm or near VUV wavelengths. Because there is some absorption of light at wavelengths near 193 nm, useful improvements in the signal level at these wavelengths can be obtained by purging all, or part of, the light path.

Figure 6:
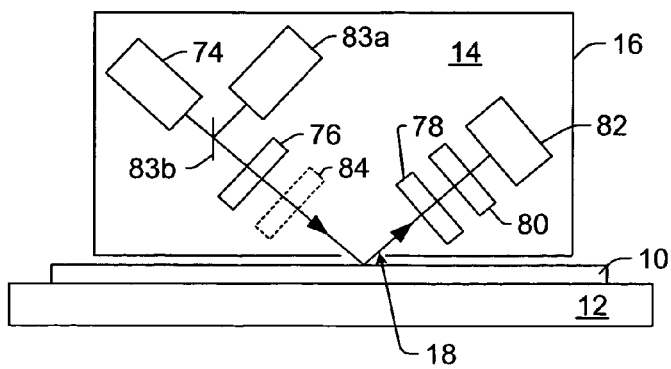
FIG. 6 is a schematic diagram illustrating a cross-sectional side view of one embodiment of an optical subsystem that includes a VUV light source and a non-VUV light source.

In some embodiments, the first optical subsystem may also be configured to perform first measurements of the specimen using VUV light and non-VUV light. In this manner, a single purged measurement light path can be used for both VUV and longer wavelengths. Such an optical subsystem may include one light source that is configured to provide both VUV light and non-YUV light. One example of such a light source is a Xenon arc lamp. Alternatively, the first optical subsystem may include two light sources, one which provides VUV light and another which provides non-VUV light. FIG. 6 illustrates one such embodiment of a first optical subsystem. Although this figure illustrates only a first optical subsystem, it is to be understood that this embodiment of the first optical subsystem may be incorporated in any of the systems described herein. As shown in FIG. 6, the first optical subsystem includes light source 74 and light source 83a. Light source 74 may be configured to provide VUV light. Light source 83a may be configured to provide non-VUV light. In such embodiments, light source 74 may include any of the light sources described above, and light source 83a may include a white light source, a laser light source, or any other non-VUV light source.

The VUV light and the non-VUV light may be combined into a single beam by dichroic mirror 83b or another suitable optical component. Therefore, the VUV light and the non-VUV light may be simultaneously directed to specimen 10 at the same incidence angle. Alternatively, the first optical subsystem may be configured to direct the VUV light and the non-VUV light to the specimen at different angles of incidence. For example, each of the light sources may be coupled to different focusing optics and/or other optical components that are configured to direct the light to the specimen. The light sources, the focusing optics, and the other optical components may be arranged such that the light from the different light sources may be directed to the specimen at different, independent angles of incidence.

Such embodiments may include filter(s) that move into the light path to limit the exposure of the specimen to VUV radiation. In one such embodiment, the first optical subsystem may include one or more filters 84, as shown in FIG. 1. Although filter(s) 84 are shown in FIG. 1 to be located between the polarizer and the specimen, it is to be understood that the filter(s) may be disposed in any location in the optical path between the light source and the specimen. The one or more filters may be configured to prevent a substantial amount of the VUV light from reaching the specimen during measurements with the non-VUV light. A selection of filters could be used, each with successively shorter cutoff wavelengths (for example, at 400 nm, 300 nm, and 190 nm) so that the specimen is exposed only to wavelengths needed for a particular measurement and no wavelengths substantially shorter than those needed. The one or more filters may include any appropriate filter(s) known in the art such as bandpass filter(s), edge filter(s), notch filter(s), or a combination thereof.

In addition, the first optical subsystem may be configured to function as multiple measurement subsystems. For example, the first optical subsystem may be configured as a spectroscopic ellipsometer as well as a single wavelength ellipsometer. In one such embodiment, the first optical subsystem may include a broadband light source configured to provide light for the spectroscopic ellipsometer. In one example, the spectroscopic ellipsometer may include a flash lamp configured to generate the VUV light. In addition, the first optical subsystem may include a monochromatic or near monochromatic light source configured to provide light for the single wavelength ellipsometer. In one particular embodiment, the single wavelength ellipsometer may include an excimer light source configured to generate light having a wavelength of about 157 nm. Such an optical subsystem may be further configured as described and illustrated in FIG. 6. Alternatively, the first optical subsystem may include a broadband light source and one or more filters coupled to the broadband light source. The filter(s) may be moved out of the optical path during operation of the first optical subsystem as a spectroscopic ellipsometer such that multiple wavelengths are directed to the specimen. The filter(s) may be moved into the optical path during operation of the first optical subsystem as a single wavelength ellipsometer. Such a first optical subsystem may be further configured as described and illustrated in FIG. 1.

Figure 7:
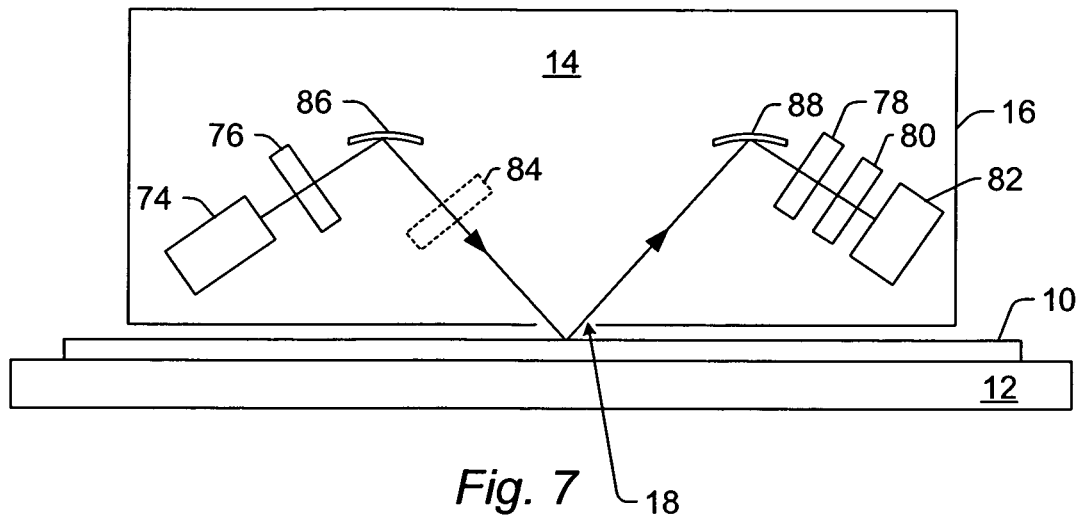
FIG. 7 is a schematic diagram illustrating a cross-sectional side view of one embodiment of an optical subsystem that includes reflective focusing optics and reflective collecting optics.
Figure 8:
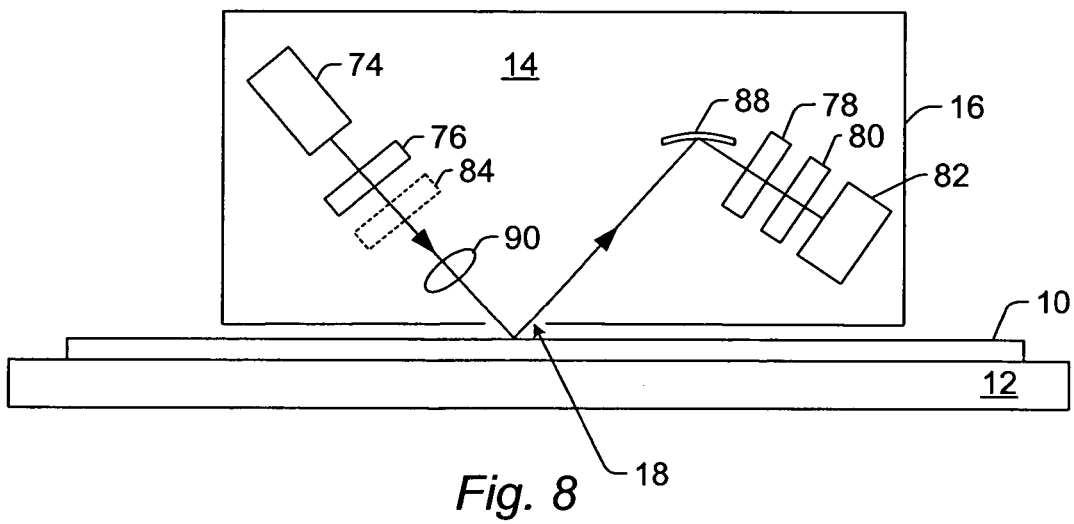
FIG. 8 is a schematic diagram illustrating a cross-sectional side view of one embodiment of an optical subsystem that includes transmissive focusing optics and reflective collecting optics.
Figure 9:
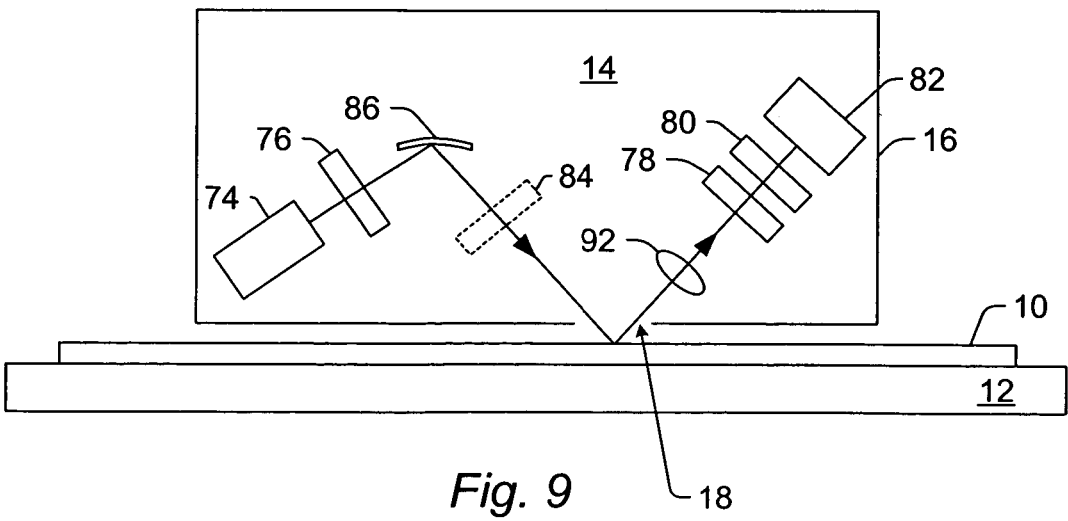
FIG. 9 is a schematic diagram illustrating a cross-sectional side view of one embodiment of an optical subsystem that includes reflective focusing optics and transmissive collecting optics.

The first optical subsystem may also include reflective or transmissive focusing optics and reflective or transmissive collecting optics. For example, FIGS. 7–9 illustrate three different embodiments of a first optical subsystem. Although these figures illustrate only a first optical subsystem, it is to be understood that these embodiments of the first optical subsystem may be incorporated in any of the systems described herein. As shown in FIG. 7, the first optical subsystem includes light source 74 and polarizer 76, which may be configured as described above. The first optical subsystem also includes reflective focusing optics 86 configured to focus light from the polarizer to specimen 10. The first optical subsystem may optionally include one or more filters 84 that are configured as described above. Although the one or more filters are shown to be placed in the optical path between reflective focusing optics 86 and specimen 10, it is to be understood that the one or more filters may alternatively be placed in any location between light source 74 and specimen 10.

This embodiment of the first optical subsystem also includes reflective collecting optics 88. Reflective collecting optics 88 may be configured to collect light from specimen 10 and to focus the collected light to polarizer 78, which may be configured as described above. The first optical subsystem may also include spectrometer 80, which may be configured as described above. In addition, the first optical subsystem includes detector 82, which may be configured as described above.

Reflective focusing optics 86 and reflective collecting optics 88 may include any focusing mirrors known in the art. Reflective focusing optics and reflective collecting optics may be particularly suitable for the VUV wavelengths of the first optical subsystem. For example, reflective optics may induce significantly less aberrations in VUV light than transmissive optics. In addition, reflective optics may be less expensive than transmissive optics that are suitable for VUV light.

However, transmissive optics may be included in the first optical subsystem. FIGS. 8 and 9 illustrate two such embodiments. For example, the embodiment of the first optical subsystem illustrated in FIG. 8 is similar to that shown in FIG. 7 except that transmissive focusing optics 90 are used in place of reflective focusing optics 86. Examples of suitable optical components for transmissive focusing optics 90 are a spherical lens, another type of lens, or a combination of lenses, each of which may be made of calcium fluoride ($CaF_2$). As shown in FIG. 8, optional one or more filters 84 may be disposed in the optical path between polarizer 76 and transmissive focusing optics 90. Alternatively, optional one or more filters 84 may be disposed in any location between light source 74 and specimen 10. The embodiment shown in FIG. 8 also includes reflective collecting optics 88, which may be configured as described above. In an alternative, the embodiment of the first optical subsystem illustrated in FIG. 9 is similar to that shown in FIG. 7 except that transmissive collecting optics 92 are used in place of reflective collecting optics 88. Transmissive collecting optics 92 may include a spherical lens, another type of lens, or a combination of lenses, each of which may be made of $CaF_2$. As further shown in FIG. 9, the first optical subsystem may include reflective focusing optics 86, which may be configured as described above. In some embodiments, the first optical subsystem may include transmissive focusing optics as shown in FIG. 8 and transmissive collecting optics as shown in FIG. 9.

In the VUV optical subsystem, the light can be transmitted from the light source to the measurement location by any means suitable for the wavelengths involved including reflection from mirrors, transmission through lenses, and transmission through hollow optical fibers. As described further herein, the use of flat mirrors or fibers can allow the measurement head to move relative to the specimen without having to move the light source.

In one embodiment, the first optical subsystem may include one or more one or more hollow optical fibers. Hollow optical fibers are defined herein as optical fibers that have at least some voided space within the optical core of the optical fibers. Hollow optical fibers may be particularly advantageous for the transmission of VUV light of the first optical subsystem since the VUV light may be substantially absorbed by the solid optical core of conventional optical fibers. Hollow optical fibers are being developed by a number of companies and organizations including, but not limited to, Bell Labs, Corning, and the University of California at Riverside.

Figure 10:
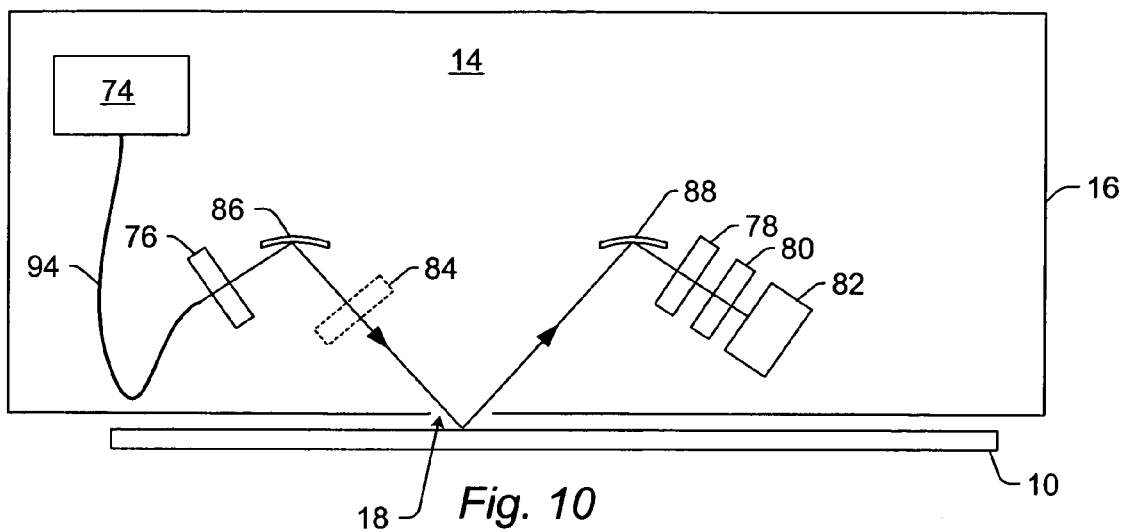
FIGS. 10 and 11 are schematic diagrams illustrating cross-sectional side views of one embodiment of an optical subsystem that includes a hollow fiber.

In one embodiment shown in FIG. 10, the first optical subsystem may include hollow optical fiber 94. Hollow optical fiber 94 is configured to direct light from light source 74 to an optical component of the first optical subsystem. For example, hollow optical fiber 94 may be configured to direct light from light source 74 to polarizer 76. The first optical subsystem is shown in this embodiment to have a similar configuration to that shown in FIG. 7. However, a hollow optical fiber may be used to transmit light from the light source to the polarizer or another optical component of any other embodiments of the first optical subsystem described herein. In some embodiments, the first optical subsystem may also include an additional hollow optical fiber (not shown). The additional hollow optical fiber may be configured to transmit light from the analyzer, the spectrometer or another optical component to the detector.

In some embodiments, the system may be configured to move the optical components of the first optical subsystem with respect to the specimen to perform the first measurements at different locations on the specimen. However, the light source may be substantially stationary during movement of the optical components. For example, as shown by comparison between FIGS. 10 and 11, the system may be configured to move polarizer 76, reflective focusing optics 86, one or more filters 84, reflective collecting optics 88, analyzer 78, spectrometer 80, and detector 82 with respect to specimen 10 such that different locations on the specimen may be measured by the first optical subsystem. However, despite the movement or different positions of these optical components, light source 74 may not be moved from its initial position. Instead, hollow optical fiber 94 may be sufficiently flexible and may have a sufficient length such that the hollow optical fiber can extend from the light source to the polarizer over a range of positions of the polarizer.

Figure 11:
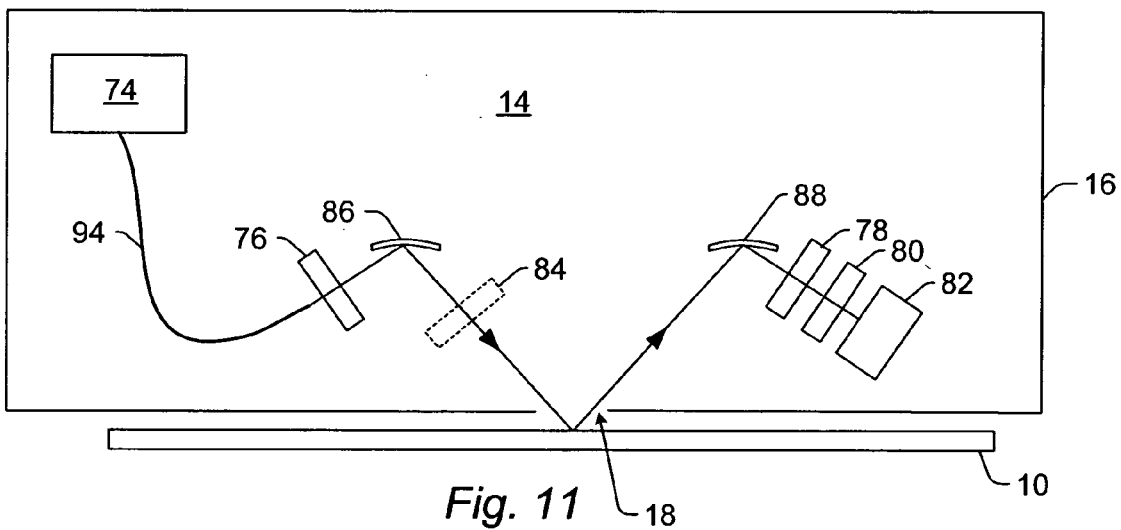

Such an embodiment may be particularly advantageous for relatively large or sensitive light sources such as excimer light sources since moving such light sources may be costly and complex. In addition, in such embodiments, the light source may be disposed outside of the purged environment within housing 16. A differential aperture in the housing may allow the hollow optical fiber to extend from the light source outside of the housing to an optical component inside the housing such as polarizer 76. Such embodiments may be particularly advantageous since the area within the housing may be reduced by moving the light source outside of the housing thereby reducing the area of the purged environment. In a similar manner, a suitable hollow optical fiber that transmits light from an optical component of the first optical subsystem to a detector may allow the detector to have a substantially stationary position during movement of the optical components. Such a configuration may be appropriate for a detector that is located inside housing 16 or outside of housing 16. Although FIGS. 10 and 11 illustrate only a first optical subsystem, it is to be understood that these embodiments of the first optical subsystem may be incorporated in any of the systems described herein.

Figure 12:
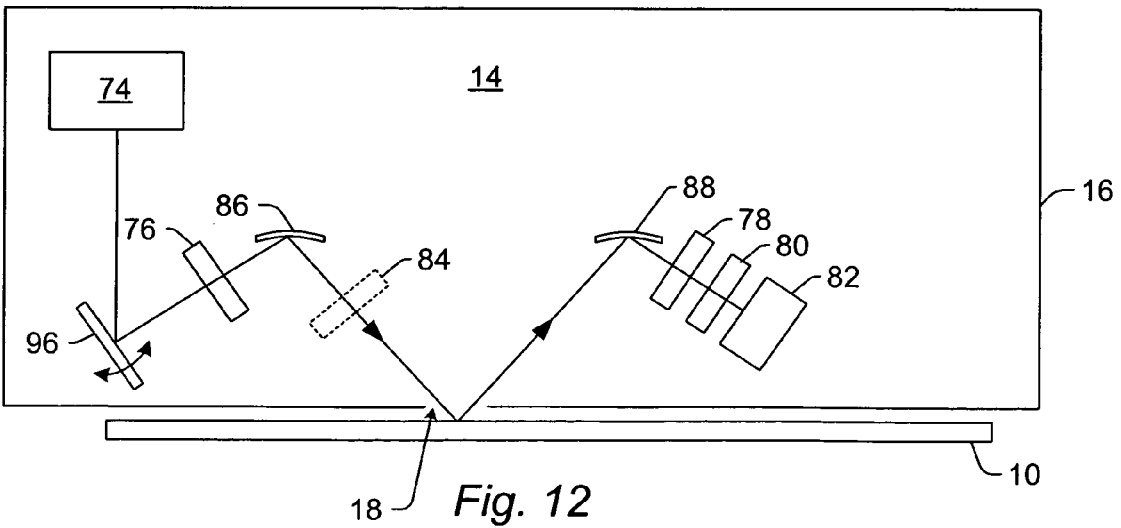
FIG. 12 is a schematic diagram illustrating a cross-sectional side view of an embodiment of an optical subsystem that includes a flat mirror and a substantially stationary light source.

In another embodiment, the first optical subsystem may include a flat mirror. One such embodiment is illustrated in FIG. 12. In this embodiment, light from light source 74 is directed to flat mirror 96. In some embodiments, light may be directed from the light source to the flat mirror by a hollow optical fiber (not shown). Flat mirror 96 directs the light from the light source to an optical component of the first optical subsystem such as polarizer 76. The flat mirror may be coupled to a mechanical assembly or other mechanism (not shown) that is configured to alter a position of the flat mirror such that the angle at which light is reflected from the flat mirror is altered. For example, the position of the flat mirror may be altered bi-directionally as shown by the vector in FIG. 12.

In this embodiment, the position of the light source may be substantially stationary. In addition, the position of flat mirror may be fixed laterally with respect to the light source. The optical components may be moved as described above to perform measurements at different locations on the specimen. To account for the different positions between the light source and these optical components, the position of the flat mirror (and optionally the position of one or more optical components such as polarizer 76) may be altered such that irregardless of the position of the optical components, the light from the light source may be directed to the appropriate optical components at the appropriate angles. Although the first optical subsystem is shown to include only one flat mirror in FIG. 12, it is to be understood that the first optical subsystem may include more than one flat mirror (not shown), each of which may be configured to reflect the light from the light source at various angles to account for movement of the optical components. Although FIG. 12 illustrates only a first optical subsystem, it is to be understood that this embodiment of the first optical subsystem may be incorporated in any of the systems described herein.

Turning back again to FIG. 1, the system shown in FIG. 1 also includes a second optical subsystem. The second optical subsystem is configured to perform second measurements of the specimen. The second optical subsystem is disposed within a non-purged environment (i.e., an ambient environment or an environment containing a substantial number of unwanted molecules) during the second measurements. For example, as shown in FIG. 1, the second optical subsystem is disposed outside of housing 16, which contains the purged environment for the first optical subsystem. In addition, although the second optical subsystem is disposed within a measurement chamber or overall housing (not shown) of the system, the measurement chamber or the overall housing is not purged. The second optical subsystem may be disposed in a non-purged environment since the second optical subsystem is configured to perform the second measurements using non-VUV light.

In the embodiment shown in FIG. 1, the second optical subsystem is configured as a reflectometer. For example, the second optical subsystem includes light source 98. Light source 98 may be a monochromatic or near monochromatic light source. In this embodiment, the reflectometer may be configured as a single wavelength reflectometer. One example of an appropriate monochromatic light source is a single wavelength laser light source. In another embodiment, the light source may be a polychromatic light source or broadband light source. In such an embodiment, the reflectometer may be configured as a spectroscopic reflectometer. One example of an appropriate broadband light source is a Xenon arc lamp that is configured to emit a light beam that includes visible and ultraviolet light.

The second optical subsystem also includes beam splitter 100. The beam splitter is configured to direct light emitted from light source 98 to specimen 10. The beam splitter may be a beam splitter mirror that can produce a continuous broadband spectrum of light. The second optical subsystem further includes lens 102, which is configured to focus light propagating from beam splitter 100 onto specimen 10. Light returned from the specimen may pass through lens 102 and beam splitter 100 to diffraction grating 104. The diffraction grating may be configured to disperse light returned from the specimen. The dispersed light may be directed to a spectrometer such as detector array 106. The detector array may include a linear photodiode array. The light may be dispersed by a diffraction grating as it enters the spectrometer such that the resulting first order diffraction beam of the sample beam may be collected by the linear photodiode array.

Although one particular configuration of a reflectometer is illustrated in FIG. 1, it is to be understood that the second optical subsystem may have any reflectometer configuration known in the art. Additional examples of spectroscopic reflectometers are illustrated in U.S. Pat. No. 4,999,014 to Gold et al. and U.S. Pat. No. 5,747,813 to Norton, which are incorporated by reference as if fully set forth herein. The second optical subsystem may also be configured as a beam profile reflectometer. Such a configuration is described further herein below.

Therefore, a plurality of optical subsystems may be used in combination in a single tool or system. However, only some of these optical subsystems (e.g., the first optical subsystem) are maintained in a purged environment. The purged environment can be created with a differential seal, such as that described by Nikoonahad et al. Preferably, the optical subsystems that are kept purged are those which use illumination sources having short wavelengths (e.g., VUV wavelengths).

The system shown in FIG. 1 includes a first optical subsystem configured as an ellipsometer and a second optical subsystem configured as a reflectometer. The ellipsometer may be disposed in a purged environment such that the ellipsometer can operate at VUV wavelengths while the reflectometer is in atmosphere and is limited to wavelengths longer than about 190 nm. Similar configurations could be envisioned for the many various configurations described in U.S. Pat. No. 6,633,831 to Nikoonahad et al., which is incorporated by reference as if fully set forth herein, and/or those combinations of subsystems present in commercially available tools from KLA-Tencor, Therma-Wave, and Rudolph Technology.

However, the system may include other combinations of optical subsystems. For example, in one embodiment, the first optical subsystem may be configured as a reflectometer, and the second optical subsystem may be configured as an ellipsometer. Such a configuration may be desirable for as system such as the F5 system commercially available from KLA-Tencor, which is described in U.S. Pat. No. 5,608,526 to Piwonka-Corle et al., which is incorporated by reference as if fully set forth herein. In particular, it might be desirable to have the reflectometer at a shorter wavelength than the ellipsometer. Therefore, it could be desirable to maintain a purged environment around just the reflectometer while permitting the ellipsometer to be exposed to an oxygen containing atmosphere.

In another example, the '752 patent referenced above describes a multi-angle ellipsometer. It is convenient to use one or more lasers as light sources for such an ellipsometer because of the brightness and stability of most lasers. Since lasers that operate at VUV wavelengths are expensive, in one preferred embodiment, a multi-angle ellipsometer with one or more visible or near infra-red lasers (such as gas or diode lasers) operating in atmosphere may be combined with a reflectometer using a VUV source such as a $D_2$ lamp. The reflectometer is purged with an inert gas utilizing a differential aperture.

In another embodiment, the first optical subsystem may be configured as an ellipsometer, a reflectometer, or another thin film measurement optical subsystem, and the first or second optical subsystem may be configured as a scatterometer. One example of an optical subsystem that may be configured as both a spectroscopic ellipsometer and a spectroscopic scatterometer is illustrated in International Publication No. WO 99/45340 to Xu et al., which is incorporated by reference as if fully set forth herein. Such an optical subsystem may be configured as described herein to perform measurements of a specimen using both VUV light and non-VUV light. The scatterometer may also have any other configuration known in the art.

The optical subsystems could be used to measure film properties and critical dimension (CD) and other shape parameters. Different wavelength ranges may be used for determining the film properties than for determining CD and other shape properties. For example, it might be advantageous to use wavelengths that extend into the VUV for optical property measurements, but use only near-UV and longer wavelengths for the CD measurements. In such an embodiment, the first optical subsystem may be configured to perform thin film measurements using the VUV light. In addition, the first or second optical subsystem may be configured to perform scatterometry measurements using the non-VUV light. In other cases with very fine structures, it might be advantageous to use VUV wavelengths for the CD measurements, but near-UV and/or longer wavelength measurements may suffice for the determination of film thickness and optical properties.

In yet another embodiment, the first optical subsystem may be configured as a spectroscopic ellipsometer or a spectroscopic reflectometer, and the second optical subsystem may be configured as a single wavelength optical subsystem. In a further embodiment, the first optical subsystem may be configured as a dual beam spectrophotometer, one configuration of which is described further below, and the second optical subsystem may be configured as a different optical subsystem. In each of these embodiments, the first optical subsystem may be disposed in a purged environment, and the second optical subsystem may be disposed in a non-purged environment. In addition, the first optical subsystem may be configured to perform measurements at VUV wavelengths, and the second optical subsystem may be configured to perform measurements at non-VUV wavelengths.

Figure 16:
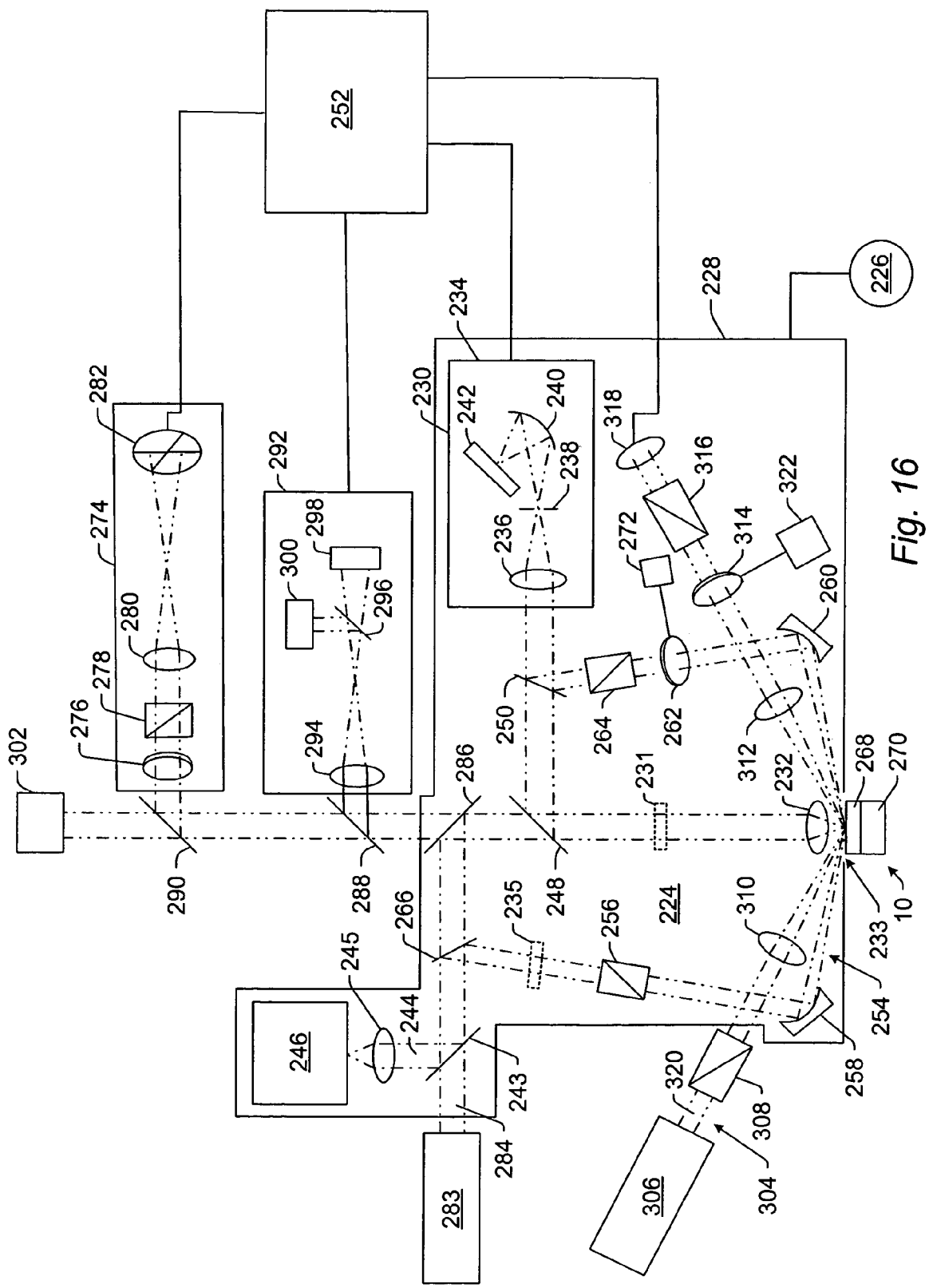

In a further embodiment, the '746 patent referenced above describes a measurement system that may incorporate up to five different measurement technologies (see, for example, FIG. 1 of the '746 patent). Three of these measurement technologies (single wavelength or "absolute" ellipsometer, beam profile reflectometer, and beam profile ellipsometer) use a laser light source operating at a wavelength that transmits through the atmosphere. The other two measurement technologies (the broadband reflectometer and the spectroscopic ellipsometer) use broadband light sources (such as a combination of a $D_2$ lamp with a quartz halogen or Xenon arc lamp). In one preferred embodiment, the system may be altered such that one, or both, of these broadband measurement technologies operates at VUV wavelengths and is contained in an inert gas environment that is separated from the atmosphere by at least one differential aperture, and is combined with at least one other measurement technology that has at least part of its light path in the atmosphere. One such embodiment is illustrated in FIG. 16, which is described in more detail below.

The system shown in FIG. 1 (and other system embodiments described herein) may also include processor 108. Processor 108 is coupled to both the first optical subsystem and the second optical subsystem by transmission media, indicated by the dotted lines. The transmission media may include wire(s), cable(s), wireless transmission path(s), network(s), or a combination thereof. The transmission media may also include "wired" and "wireless" portions. Although processor 108 is shown to be directly coupled to the first optical subsystem and the second optical subsystem (e.g., directly coupled to detector array 106 of the second optical subsystem), it is to be understood that the processor may be indirectly coupled to the first and/or second optical subsystems through one or more intermediate components such as electronics or local processors.

Processor 108 may perform one or more functions on data generated by the first and second optical subsystems. In one embodiment containing multiple measurement technologies, one measurement technology may be used to calibrate other measurement technologies. The reference metrology technology is used to calibrate other technologies including those operating in the purged environment or at VUV wavelengths. For example, the system may be configured to calibrate the first optical subsystem with data generated by the second optical subsystem. Processor 108 may perform at least a portion of that calibration. If the system is configured to calibrate the first optical subsystem with data generated by the second optical subsystem, then the second optical subsystem is preferably a substantially accurate and stable subsystem. For example, in one such embodiment, the second optical subsystem may be configured as a single wavelength ellipsometer. In an alternative embodiment, the second optical subsystem may be configured as a beam profile reflectometer. Such second optical subsystems may include a laser light source, which is advantageous for calibration because of the stability of the laser.

In an additional embodiment, the processor may be configured to use data generated by the first optical subsystem to determine one or more properties of the specimen. For example, an intensity of light at the elements of the detector array may be converted by the processor to ellipsometric parameters, $\psi$ and $\Delta$, by mathematical equations known in the art. The ellipsometric parameters may be typically shown as tan $\psi$ and cos $\Delta$. Tan $\psi$ is the amplitude of the complex ratio of the s and p components of the reflectivity of the sample, and $\Delta$ is the phase of the complex ratio of the s and p components of the reflectivity of the sample. The term "s component" is used to describe the component for the polarized radiation having an electrical field perpendicular to the plane of incidence of the reflected beam. The term "p component" is used to describe the component for the polarized radiation having an electrical field in the plane of incidence of the reflected beam. For very thin films, tan $\psi$ may be independent of thickness, and $\Delta$ may be linearly proportional to the thickness.

Software integrated into the processor may be configured to convert the ellipsometric parameters, $\psi$ and $\Delta$, to an optical property of a specimen using a mathematical, or optical, model. Typically, a personal computer having a software package operable to rapidly performing data-fitting calculations such as a least-squares fitting technique may be appropriate for this use. Because ellipsometric parameters including $\psi$ and $\Delta$ may be determined at small increments across a broad spectrum of wavelengths and at several angles, several hundred data points may be included in the calculations. Several software packages configured for use with spectroscopic ellipsometers that are capable of handling such a large amount of data are commercially available.

There are several optical models that may be used to analyze ellipsometric data. Examples, of such models include, but are not limited to, a cauchy model, a harmonic oscillator model, and a polynomial series expansion model. An appropriate model may be chosen based on specimen characteristics, desired optical properties of the specimen, and the computational difficulty associated with the model. For example, the cauchy model is a relatively straightforward mathematical model. The cauchy model, however, may not be valid for wavelengths at which a specimen exhibits absorption. Additionally, optical properties of several layers of a specimen may also be determined simultaneously by using an appropriate optical model or a combination of optical models. Therefore, when using spectroscopic ellipsometry to analyze a specimen, one or more optical models may be more appropriate for analysis than others.

Thicknesses, indexes of refraction, and extinction coefficients (which are commonly referred to as "thin film measurements") for a layer of a specimen, a portion of a layer of a specimen, or several layers of a specimen may be determined from ellipsometric parameters using an optical model. The index of refraction, "n," is related to the speed of light as it moves through a medium and is dependent upon the wavelength of the light. The extinction coefficient, "k," is also dependent upon wavelength and relates to absorption of light by a medium. The extinction coefficient may also be used to determine the absorption coefficient for a given wavelength. Further discussion of the ellipsometric parameters and the optical properties of materials is illustrated in U.S. Pat. No. 4,905,170 to Forouhi, et al., which is incorporated by reference as if fully set forth herein.

In another embodiment, the processor may be configured to use data generated by the second optical subsystem to determine one or more properties of the specimen. For example, the photodiode array of detector array 106 may measure the reflectance spectrum of the light returned from the surface of the specimen. The relative reflectance spectrum may be obtained by dividing the intensity of the returned light of the reflectance spectrum at each wavelength by a relative reference intensity at each wavelength. A relative reflectance spectrum may be used to determine the thickness of various films on the specimen. In addition, the reflectance at a single wavelength and the refractive index of the film may also be determined from the relative reflectance spectrum. Furthermore, a model method by modal expansion (MMME) model may be used to generate a library of various reflectance spectrums. The MMME model is a rigorous diffraction model that may be used to calculate the theoretical diffracted light "fingerprint" from each grating in the parameter space. Alternative models may also be used to calculate the theoretical diffracted light, however, including, but not limited to, a rigorous coupling waveguide analysis (RCWA) model. The measured reflectance spectrum may be fitted to the various reflectance spectrums in the library. The fitted data may also be used to determine a critical dimension such as a lateral dimension, a height, and/or a sidewall angle of a feature on the specimen. Processor 108 may be configured to perform all of the above calculations. Examples of modeling techniques are illustrated in International Application No. WO 99/45340 to Xu et al., which is incorporated by reference as if fully set forth herein.

In a further embodiment, where one of the optical subsystems is configured as a scatterometer (e.g., a single wavelength scatterometer or a spectroscopic scatterometer), the processor may be configured to use data from the scatterometer to determine one or more properties of the specimen. The properties may include a critical dimension, a height, and/or a sidewall angle of a feature on the specimen. Examples of how such properties can be determined from scatterometry data are illustrated in International Publication No. WO 99/45340 to Xu et al. and U.S. patent application Ser. No. 09/927,102 to Weber-Grabau et al., which are incorporated by reference as if fully set forth herein. Alternatively, or in addition, the properties may include an overlay measurement of the specimen. Overlay generally refers to a lateral position of a feature on one level of a wafer with respect to a lateral position of a feature on another level of the wafer. Examples of how overlay can be determined from scatterometry data are illustrated in U.S. patent application Ser. No. 09/927,102 to Weber-Grabau et al. and International Publication No. WO 02/25723 to Brill et al., which are incorporated by reference as if fully set forth herein.

In any situation where a measurement system incorporates more than one measurement technology and where at least one of those technologies operates at a VUV wavelength, it may be advantageous to combine a measurement made at one or more VUV wavelengths with a measurement made at one or more non-VUV wavelengths in order to get better measurement results than can be obtained by either wavelength ranges alone. In one embodiment, the system may be configured to use data generated by the first and second optical subsystems in combination to determine one or more properties of the specimen. The determinations may be performed by the processor. For example, the processor may be configured to perform a computer-implemented method for analysis of a specimen. The method includes determining one or more properties of the specimen using first data in combination with second data. The first data is measured at a VUV wavelength, and the second data is measured at a non-VUV wavelength. For example, the first data may be measured with the first optical subsystem, which is disposed within a purged environment in the system. The second data may be measured with the second optical subsystem. The first and second optical subsystems may be disposed in a single system as described herein, and the second optical subsystem may be disposed within a non-purged environment in the system. Alternatively, the first and second data may be measured with the first optical subsystem, which is disposed within a purged environment in the system.

There are many ways to do such combining, including using all the measurements as constraints with appropriate relative weighting in a non-linear regression, or by using one wavelength range from one measurement technology to first determine one parameter such as thickness and then using another wavelength range from another measurement technology to determine another parameter or parameters such as refractive index. In addition, genetic algorithms can be used to combine the results from multiple measurement subsystems. Many different algorithms can be used individually or in combination to extract the results from the data. In one embodiment, the one or more properties may be determined using one or more algorithms. The one or more algorithms may include a genetic algorithm, a non-linear regression algorithm, a comparison algorithm (e.g., comparison with a database (or library) or pre-computed or pre-measured results), or a combination thereof. Many such algorithms are known in the art, and the processor may use any of these algorithms to determine the one or more properties. Examples of genetic algorithms are illustrated in U.S. Pat. No. 5,953,446 to Opsal et al. and U.S. Pat. No. 6,532,076 to Sidorowich, which are incorporated by reference as if fully set forth herein. In one embodiment, the first and second data may include scatterometry data. In such an embodiment, it may be particularly advantageous to determine the one or more properties of the specimen using one or more genetic algorithms.

If it is desired to know the thickness of a film on a substrate and its optical properties such as refractive index, n, and absorption, k, at a VUV wavelength such as 157 nm, a better measurement result may be obtained by combining a measurement made with a visible wavelength, which might give a more accurate measurement of film thickness, with a measurement made at VUV wavelengths rather than using just VUV wavelengths. In this manner, the second data may be used to determine a thickness of a structure on a specimen. This thickness may be used in combination with the first data to determine the optical properties of the structure at one or more VUV wavelengths.

In a different embodiment, the one or more properties may include an atomic concentration of one or more structures on the specimen. In one such embodiment, the atomic concentration may be determined from optical properties of the one or more structures. In this manner, the atomic concentration may be inferred indirectly from the optical properties (such as n and/or k). The optical properties may be determined from the first data, the second data, or the first and second data. In an alternative embodiment, the atomic concentration may be determined by comparison of the first and second data with reference data. In this manner, the atomic concentration may be determined directly by comparison with results from previously measured samples. Materials that may be of interest for atomic concentration measurements include, but are not limited to, carbon, nitrogen, oxygen, cobalt, nickel, titanium, zirconium, hafnium, tantalum, tungsten, rhenium, silicon, germanium, and various transition and rare-earth metals.

The one or more properties that are determined from the first and second data may include other properties of the specimen such as, but not limited to, optical properties of an upper layer on the specimen, optical properties of more than one layer on the specimen, critical dimension (CD) of a feature on the specimen, shape parameters of the feature on the specimen, overlay offset between two layers on the specimen, or a combination thereof.

The processor may also be configured to perform other metrology and/or inspection functions on the data generated by the first and/or second optical subsystems. For example, the processor may be configured to detect defects on the specimen using data from the first and/or second optical subsystem. The processor may detect defects on the specimen using any algorithm or method known in the art such as a thresholding algorithm or a die-to-die comparison method.

Metrology methods and systems are also provided for nitrided oxide gate film process monitoring and process control for semiconductor device fabrication. Several methods for nitrided oxide gate film process monitoring and control are currently used. For example, methods that may be used for nitrogen concentration and dose measurements include x-ray photoemission spectroscopy (XPS) and secondary ion-emission mass spectroscopy (SIMS). There are, however, several disadvantages to the currently used methods. In addition, this measurement technique has relatively poor thickness accuracy and repeatability. Furthermore, XPS is generally slow, expensive (e.g., about $300 per analysis), and not capable of fast, in-line process monitoring and control in a high volume semiconductor manufacturing application. Similarly, SIMS is also destructive in that the wafer must be broken and the film being analyzed is damaged. In addition, this measurement technique has relatively poor thickness accuracy and repeatability and is not suitable for high volume semiconductor manufacturing applications.

Embodiments of a method for measurement of a nitrided oxide gate dielectric described herein may or may not include forming a nitrided oxide gate dielectric on a specimen. The specimen in such embodiments is a wafer. In general, a nitrided oxide gate dielectric is formed on a wafer by exposing an oxygen-containing layer such as silicon dioxide to a nitrogen-containing plasma. Examples of methods for forming a nitrided oxide on a wafer are illustrated in U.S. Pat. No. 6,555,485 to Liu et al., U.S. Pat. No. 6,559,007 to Weimer, U.S. Pat. No. 6,610,614 to Niimi et al., and U.S. Pat. No. 6,610,615 to McFadden et al., which are incorporated by reference as if fully set forth herein. A nitrided oxide gate dielectric may also be formed on a wafer using any other method known in the art.

In one embodiment, a method for measurement of a specimen is provided. The method includes measuring spectroscopic ellipsometric data of the specimen. The spectroscopic ellipsometric data may be measured using one of the optical subsystems described herein. In one embodiment, the spectroscopic ellipsometric data may be measured at wavelengths from about 220 nm to about 900 nm. In a different embodiment, the spectroscopic ellipsometric data may be measured at wavelengths from about 190 nm to about 300 nm. In such embodiments, the spectroscopic ellipsometric data may be measured using one of the non-VUV optical subsystems described herein. In one particular example, ellipsometry spectra of the specimen can be acquired using KLA-Tencor's SpectraFx100 spectroscopic ellipsometry subsystem at wavelengths from about 220 nm to about 900 nm, or a combination of spectroscopic ellipsometer and deep ultraviolet spectroscopic ellipsometer subsystems at wavelengths from about 190 nm to about 300 nm. Alternatively, the spectroscopic ellipsometric data may be measured at VUV wavelengths. In this manner, the spectroscopic ellipsometric data may be measured using one of the VUV optical subsystems described herein.

In other embodiments, the spectroscopic ellipsometric data may be measured at VUV and non-VUV wavelengths. In such embodiments, the spectroscopic ellipsometric data may be measured using one optical subsystem or two different optical subsystems. For example, one optical subsystem that is configured to operate at VUV and non-VUV wavelengths may be used to measure the spectroscopic ellipsometric data. If the data is measured by two different optical subsystems (one VUV and one non-VUV), the data may be combined into one data set and then used to determine a property of the nitrided oxide gate dielectric.

In addition, the method includes determining a nitrogen concentration of a nitrided oxide gate dielectric formed on the specimen from the spectroscopic ellipsometric data. The nitrogen concentration may be determined as described above with respect to atomic concentration measurements. For example, the method may include determining an index of refraction of the nitrided oxide gate dielectric from the spectroscopic ellipsometric data and determining the nitrogen concentration from the index of refraction. In a particular example, a quantitative correlation between the measured index of refraction or index of refraction model (e.g., the BEMA fraction) and the nitrogen concentration may be determined using measurements of specimens having known nitrogen concentration values. The quantitative correlation may then be used to determine the nitrogen concentration of other specimens based on a measured index of refraction.

Preferably, measurement of ellipsometry spectra of nitrided oxide gate dielectric films is performed over a broad range of wavelengths such that the film thickness and index of refraction can be determined from the spectra. Therefore, in some embodiments, the method may also include determining a thickness and an index of refraction of the nitrided oxide gate dielectric using the spectroscopic ellipsometric data. In addition, the thickness and index of refraction of a nitrided oxide gate dielectric may be measured simultaneously, which may be particularly advantageous due to the strong correlation effect between the thickness and index of refraction measurements of thin films. In contrast, in the past, as a general practice, only the thickness could be measured for films thinner than 100 angstroms.

In one embodiment, the method may also include measuring reflectometric data of the specimen. The reflectometric data may be measured at a single wavelength or at multiple wavelengths (e.g., spectroscopic reflectometric data). The reflectometric data may be measured using one of the optical subsystem embodiments described herein that is configured as a reflectometer or spectroscopic reflectometer. In addition, the spectroscopic ellipsometric data and the reflectometric data may be measured with one system (e.g., different optical subsystems arranged within a single system). The reflectometric data may be measured at non-VUV wavelength(s), VUV wavelength(s) or non-VUV and VUV wavelengths.

In some embodiments, the nitrogen concentration of the nitrided oxide gate dielectric may be determined from the spectroscopic ellipsometric data in combination with the reflectometric data. For example, the reflectometric data may be used to determine a thickness of a nitrided oxide. The thickness and the spectroscopic ellipsometric data may be used in combination to determine an index of refraction of the nitrided oxide, and the index of refraction may be used to determine the nitrogen concentration.

In some embodiments, measuring the spectroscopic ellipsometric data may include measuring the data at multiple locations on the specimen. In such embodiments, the method may also include determining the nitrogen concentration at the multiple locations and determining a within wafer (WIW) uniformity of the nitrogen concentration. In other words, the nitrogen concentration versus location on the specimen may be determined.

In additional embodiments, the method may include removing contaminants (e.g., air-borne molecular contamination (AMC)) from a localized area on the specimen using a laser-based cleaning subsystem prior to measurements of the specimen. The laser-based cleaning subsystem may be configured as described further herein. In addition, the laser-based cleaning subsystem may be arranged in one single system that also includes the optical subsystem that is used for measuring spectroscopic ellipsometric data of the specimen. Such configurations of a system are described further herein. Removing contaminants from a specimen just prior to the measurements may substantially increase the accuracy of the measurements particularly for substantially thin nitrided oxide gate dielectrics.

Measuring the spectroscopic ellipsometric data of the specimen may be performed during a semiconductor fabrication process. In other words, the spectroscopic ellipsometric measurements may be performed in-situ. In one embodiment, the spectroscopic ellipsometric data may be measured after or between individual processes involved in the semiconductor fabrication process (e.g., after formation of the nitrided oxide gate dielectric). Alternatively, the spectroscopic ellipsometric data may be measured during an individual process involved in the semiconductor fabrication process (e.g., during formation of the nitrided oxide gate dielectric).

In such embodiments, one of the optical subsystems described herein or another spectroscopic ellipsometer subsystem, and optionally a reflectometer subsystem, may be coupled to a semiconductor fabrication process tool. For example, for spectroscopic ellipsometric measurements of a nitrided oxide gate dielectric, a spectroscopic ellipsometer optical subsystem may be coupled to a plasma nitridation process tool. However, any of the optical subsystems or systems described herein may be coupled to any other semiconductor fabrication process tool known in the art (e.g., a lithography tool, a deposition tool, an anneal tool, an etch tool, a cleaning tool, a chemical-mechanical polishing tool, a plating tool, an ion implantation tool, etc.). Examples of how an optical subsystem or a measurement system may be coupled to a semiconductor fabrication process tool are described in U.S. Pat. No. 6,633,831 to Nikoonahad et al., which is incorporated by reference as if fully set forth herein.

The method may also include monitoring one or more parameters of a semiconductor fabrication process using the nitrogen concentration. For example, the nitrogen concentration may be measured repeatedly over time on many different specimens and the nitrogen concentration values and variations may be recorded. The data may then be used to determine changes in parameter(s) of the process. In particular, the nitridation process (or individual processes involved in the nitridation process) may be monitored using the nitrogen concentration. Parameter(s) of a semiconductor fabrication process may also, or alternatively, be monitored using other properties of the nitrided oxide gate dielectric that are determined as described herein (e.g., the WIW uniformity, thickness, and/or index of refraction of the nitrided oxide gate dielectric). For example, monitoring the parameter(s) of a semiconductor fabrication process may be performed using the index of refraction (n) of the nitrided oxide gate dielectric at a given wavelength (e.g., at 193 nm, at 248 nm, at 633 nm) or an index of refraction model parameter (e.g., the BEMA fraction in a Bruggermann Effective Media Approximation model) for process control instead of the nitrogen concentration.

In addition, the method may include altering one or more parameters of a semiconductor fabrication process based on the nitrogen concentration. In some embodiments, the parameter(s) may also, or alternatively, be altered based on the WIW uniformity, thickness, and/or index of refraction of the nitrided oxide gate dielectric. Preferably, the parameter(s) that are altered are parameter(s) of a nitridation process or individual processes involved in forming the nitrided oxide gate dielectric (e.g., a thermal oxidation process, a nitridation process, an anneal process, etc.). The parameter(s) may be altered using a feedback technique (e.g., if the nitrogen concentration is measured after the nitridation process) and/or using an in situ control technique (e.g., if the nitrogen concentration is measured during the nitridation process).

The parameter(s) are preferably altered to make differences between the measured nitrogen concentration and a target nitrogen concentration smaller. Since the nitrogen concentration can be measured during the semiconductor fabrication process, the parameter(s) of the process can be altered in response to the nitrogen concentration much more quickly than if the other measurement techniques described above (e.g., XPS and SIMS) were used to measure the nitrogen concentration. Therefore, the methods described herein may provide more accurate process control and may increase yield and throughput of the semiconductor manufacturing process. In addition, the parameter(s) that are altered may be parameter(s) of one or more processes performed on the specimen upon which the measured nitrided oxide is formed. The parameter(s) may be altered, in this embodiment, using a feedforward control technique.

Altering the parameter(s) of the semiconductor manufacturing process may be performed manually (e.g., by an operator) or automatically by a processor. The processor may be configured as described herein. The processor may also be coupled to a semiconductor manufacturing process tool. In this manner, the processor may send the changes for the parameter(s) to the semiconductor manufacturing process tool. A processor of the semiconductor manufacturing tool may then make the appropriate changes to the process (es).

The embodiments of the methods described herein for measurement or determination of nitrogen concentration have many advantages over the currently used methods. For example, the above described methods are relatively fast (e.g., each measurement takes about 5 seconds to about 15 seconds to report results). The above described methods also have relatively high accuracy (e.g., error for thickness measurements of less than about 1.0 angstrom and error for nitrogen concentration of less than about 2 at %). Furthermore, the methods for nitrogen concentration measurement or determination described herein have better repeatability (e.g., for 3 sigma, 0.15 angstroms for thickness and 0.5 at % for nitrogen concentration) than currently used methods (e.g., for XPS and 3 sigma, 1 angstrom for thickness and 1.0% for nitrogen concentration).

In addition, the above described methods are non-destructive. Therefore, the nitrogen concentration of product wafers may be measured thereby providing substantially more accurate process monitoring and control since measurements do not have to be performed on monitor wafers that are different than actual product wafers. Moreover, the methods for nitrogen concentration measurement described herein can be used for high-volume semiconductor device fabrication using commercially available optical subsystems such as KLA-Tencor's F5x and SpectraFx100 metrology tools. In particular, the methods may be applied to 90 nm, 65 nm, and possibly 45 nm generation logic and DRAM devices. Therefore, the methods provide solutions for fast, accurate, stable, and cost effective methods to monitor and control the nitrided gate process in development and volume manufacturing.

Additional embodiments relate to a computer-implemented method for analysis of a specimen. The method includes determining a nitrogen concentration of a nitrided oxide gate dielectric formed on the specimen from spectroscopic ellipsometric data generated by measurement of the specimen. The spectroscopic ellipsometric data may be measured as described above. For example, the spectroscopic ellipsometric data may be measured at wavelengths from about 220 nm to about 900 nm. Alternatively, the spectroscopic ellipsometric data may be measured at wavelengths from about 190 nm to about 300 nm. In another alternative, the spectroscopic ellipsometric data may be measured at VUV wavelengths. In an additional embodiment, the spectroscopic ellipsometric data may be measured at multiple locations on the specimen. The method may also include determining the nitrogen concentration at the multiple locations and determining a WIW uniformity of the nitrogen concentration.

In some embodiments, the method may include determining an index of refraction of the nitrided oxide gate dielectric from the spectroscopic ellipsometric data and determining the nitrogen concentration from the index of refraction as described above. In another embodiment, the method may include determining a thickness and an index of refraction of the nitrided oxide gate dielectric using the spectroscopic ellipsometric data. In other embodiments, determining the nitrogen concentration may include determining the nitrogen concentration from the spectroscopic ellipsometric data in combination with reflectometric data generated by measurement of the specimen.

In additional embodiment, the method may include determining one or more parameters of a semiconductor fabrication process based on the nitrogen concentration and/or other determined properties of the nitrided oxide gate dielectric. The method may also include altering the one or more parameters of the semiconductor fabrication process based on the determined parameter(s). The parameter(s) may be altered as described above. In further embodiments, the method may include monitoring one or more parameters of a semiconductor fabrication process using the nitrogen concentration and/or other determined properties of the nitrided oxide gate dielectric. The parameter(s) of the semiconductor fabrication process may be monitored as described above.

Program instructions implementing methods such as those described herein may be transmitted over or stored on a carrier medium. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape.

In an embodiment, a processor may be configured to execute the program instructions to perform a computer-implemented method according to the above embodiments. The processor may take various forms, including a personal computer system, mainframe computer system, workstation, network appliance, Internet appliance, personal digital assistant ("PDA"), television system or other device. In general, the term "computer system" may be broadly defined to encompass any device having a processor, which executes instructions from a memory medium.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

Figure 13:
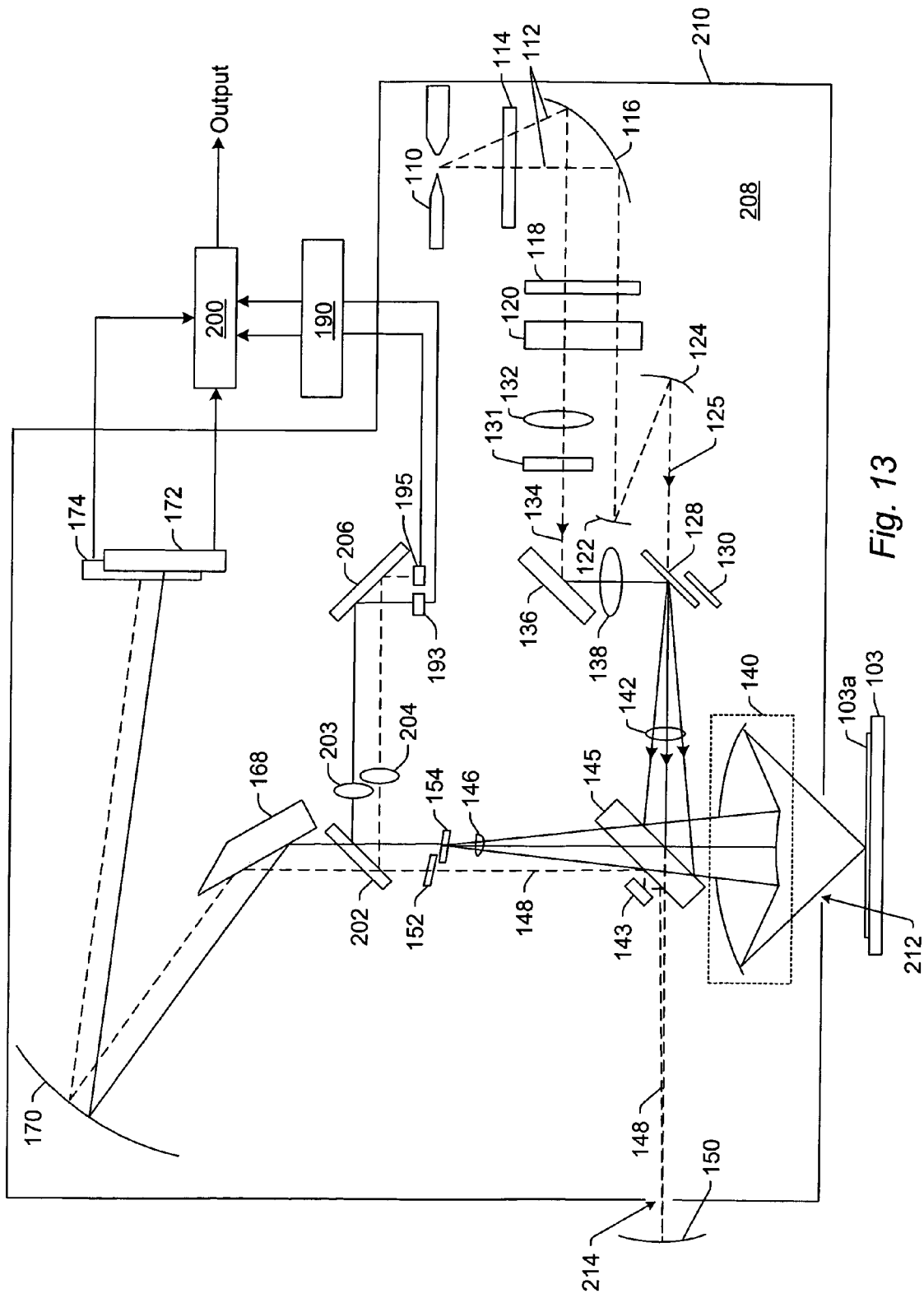
FIG. 13 is a schematic diagram illustrating a cross-sectional side view of an embodiment of a dual channel optical subsystem and a purged environment around the dual channel optical subsystem.

FIG. 13 illustrates another embodiment of an optical subsystem that may be included in a system for measurement of a specimen. In this embodiment, the optical subsystem is configured as a dual channel optical subsystem such as a dual beam spectrophotometer. This optical subsystem may be included in the systems described herein as either a first optical subsystem or a second optical subsystem. This configuration is described in more detail in U.S. Pat. No. 5,486,701 to Norton et al. and U.S. Pat. No. 5,608,526 to Piwonka-Corle et al., which are incorporated by reference as if fully set forth herein. For the sake of clarity, some of the components and details of the system have been omitted from FIG. 13 and the corresponding description presented herein. However, it is to be understood that the system illustrated in FIG. 13 may be further configured as described in this patent.

The optical subsystem may include lamp 110 (typically a Xenon arc lamp) which emits radiation beam 112 (including visible and/or UV radiation), lamp housing window 114, off-axis paraboloid mirror 116, flip-in UV cutoff filter 118, color filter wheel 120, flat mirror 122, concave mirror 124, aperture mirror 128 with flip-in forty-micron fine focus aperture 130, large achromat 132, field illumination shutter 131, fold mirror 136, and small achromat 138, as described in U.S. Pat. No. 5,486,701.

In an alternative embodiment, the optical subsystem may include a light source that can generate VUV light. In some embodiments, the optical subsystem may include a light source that can generate VUV light as well as non-VUV light or two light sources, one that can generate VUV light and another that can generate non-VUV light. Examples of suitable light sources that can generate such light are described further above. Therefore, the dual channel optical subsystem can perform measurements of the specimen using VUV light, non-VUV light, or a combination thereof. If the optical subsystem is configured to perform measurements using VUV light and non-VUV light, the dual channel optical subsystem may include one or more filters (not shown) configured to prevent a substantial amount of the VUV light from reaching the specimen during the additional measurements with the non-VUV light. The one or more filters may be located in a variety of places in the optical path of the dual channel optical subsystem between light source 110 and objective 140. The one or more filters may be further configured as described above.

The components described above provide combined beam 142 including measurement beam 125 and field illumination beam 134. Off-axis paraboloid mirror 116 collimates beam 112, which can be optionally filtered by flip-in UV cutoff filter 118 and color filter wheel 120. Flip-in UV cutoff filter 118 is used in part to limit the spectrum of beam 112 so that when beam 112 is dispersed by a diffraction grating, the first and second order diffraction beams do not overlap. Part of beam 112 is reflected by flat mirror 122 onto concave mirror 124 to form measurement beam 125. Mirror 124 focuses an image of the arc onto aperture mirror 128. The radiation emanating from each point in the image of the arc expands in a uniform cone, typically producing a uniform circle of illumination at beam divider 145.

Another part of beam 112, field illumination beam 134, is focused by large achromat 132 near fold mirror 136, causing fold mirror 136 to reflect an image of lamp 110 toward small achromat 138. Small achromat 138 collects the radiation in beam 134 before it reflects from aperture mirror 128. The aperture is placed at one conjugate of objective 140. The field illumination can be turned off by placing field illumination shutter 131 in the optical path of field illumination beam 134.

Narrow measurement beam 125 and wide field illumination beam 134 are rejoined at aperture mirror 128, with field illumination beam 134 reflecting off the front of aperture mirror 128, and measurement beam 125 passing through the aperture. The optical subsystem includes objective 140, beamsplitter mirror 145, sample beam 146, reference beam 148, concave mirror 150, flat mirror 143, reference plate 152 with a reference spectrometer pinhole therethrough, sample plate 154 with a sample spectrometer pinhole therethrough, second fold mirror 168, diffraction grating 170, sample linear photodiode array 172, reference linear photodiode array 174, reference photodiode 195, and sample photodiode 193. Objective 140, which can be a reflective objective (as shown in FIG. 13) or a transmissive objective (not shown) preferably has several selectable magnifications. Therefore, the optical subsystem may include reflective focusing optics or transmissive focusing optics.

The measurement of the relative reflectance spectrum of a specimen, which in this case is shown as wafer 103, will now be described. When field illumination shutter 131 is placed in the path of field illumination beam 134, combined beam 142 includes only measurement beam 125. Combined beam 142 is split by beam splitter mirror 145, a totally reflecting mirror placed so as to deflect half of combined beam 142 towards objective 140, thus forming sample beam 146, the undeflected half of combined beam 142 forming reference beam 148. Importantly, because sample beam 146 and reference beam 148 are derived from the same source (lamp 110) and because combined beam 142 is radially uniform, reference beam 148 and sample beam 146 have proportionally dependent spectral intensities. Furthermore, since beamsplitter mirror 145 is a totally reflecting mirror in half of the optical path rather than a partially reflecting mirror in the entire optical path, a continuous broadband spectrum is reflected with good brightness.

Reference beam 148 does not initially interact with beamsplitter mirror 145, but instead illuminates concave mirror 150. Concave mirror 150 is slightly off-axis, so reference beam 148 is reflected onto the reverse face of beamsplitter mirror 145, and flat mirror 143 re-reflects reference beam 148 into alignment with the reference spectrometer pinhole through plate 152. Flat mirror 143 is provided to realign reference beam 148 with sample beam 146 so that both beams pass though their respective spectrometer pinholes substantially parallel.

The focal length of concave mirror 150 is such that reference beam 148 is in focus at the reference spectrometer pinhole (which extends through plate 152). The radiation passing through the reference spectrometer pinhole and reflecting from fold mirror 168 is dispersed by diffraction grating 170. The resulting first order diffraction beam is collected by reference linear photodiode array 174, thereby measuring a reference reflectance spectrum.

Sample beam 146 is reflected from beamsplitter mirror 145 towards objective 140, which focuses sample beam 146 onto wafer 103, and the reflected sample beam 146 is focused by objective 140 onto the sample spectrometer pinhole (which extends through plate 154). As described above, objective 140 may be a transmissive objective or a reflective objective. Therefore, the optical subsystem may include either reflective collecting optics or transmissive collecting optics. However, since objective 140 both focuses the light on the specimen and collects the light returned from the specimen, the focusing and collecting optics are either transmissive or reflective. However, it is to be understood that the optical subsystem shown in FIG. 13 may alternatively include reflective focusing optics and transmissive collecting optics or vice versa. For example, the optical subsystem may be configured to use separate optics for focusing light on the specimen and for collecting light from the specimen. In this manner, the optical subsystem may include reflective focusing optics and transmissive collecting optics. Alternatively, the optical subsystem may include transmissive focusing optics and reflective collecting optics.

The reflected sample beam 146 does not interact with beamsplitter mirror 145 on the reflected path, because sample beam 146 passes through the space behind beamsplitter mirror 145, through which reference beam 148 also passes. The radiation passing through the sample spectrometer pinhole and reflecting from fold mirror 168 is dispersed by diffraction grating 170. As with the reference beam, the resulting first order diffraction beam of the sample beam is collected by sample linear photodiode array 172, thereby measuring the sample spectrum.

The relative reflectance spectrum can be simply obtained by processing the outputs of arrays 172 and 174 in processor 200, by dividing the sample light intensity at each wavelength (the output of array 172) by the reference intensity at each wavelength (the output of array 174).

In some embodiments, diffraction grating 170 is a concave holographic grating and the spectrometer pinholes (through plates 152 and 154) are 15 mm apart. This embodiment of diffraction grating 170 is holographically corrected to image multiple spectra, since the 15 mm spacing does not allow for both beams to be centered on the grating. It is also desirable that grating 170 be designed so that the angle of detectors 172 and 174 causes reflections from the detectors to propagate away from the grating.

In an operating mode for measuring the thickness of very thin film 103a (VTF 103a) on sample 103, the system employs sample VTF photodiode 193 and reference VTF photodiode 195. Dichroic mirror 202 mounted on a moveable arm flips into the beam path immediately beyond apertured plates 152 and 154. The dichroic mirror reflects UV radiation (with wavelength between 400 nm and 280 nm) and transmits visible light. The reflected UV from the reference beam is focused by fused silica lens 204, reflected by fixed dichroic mirror 206, and finally falls on UV enhanced silicon photodiode 195 (the "reference VTF photodiode"), and the reflected UV from the sample beam is focused by fused silica lens 203, reflected by fixed dichroic mirror 206, and finally falls on UV enhanced silicon photodiode 203 (the "sample VTF photodiode"). Second dichroic mirror 206 is needed to filter out residual visible light.

The radiation transmitted through first dichroic 202 continues through the normal spectrometer path.

In a new embodiment, if the dual channel optical subsystem is configured to perform measurements with VUV light in addition to non-VUV light, dichroic mirror 202 may be configured to reflect VUV radiation and transmit non-VUV radiation. In such an embodiment, fused lenses 203 and 204 may be replaced with calcium fluoride lenses. Such an embodiment may be further configured as described above.

Each of photodiodes 193 and 195 measures a single intensity value, but typically this value is an average over a broadband frequency range of interest (in the UV range) so that the two photodiodes provide sufficient information for calculating a relative reflectance (or reflectance) value representing an average over such broadband frequency range. Photodiodes 193 and 195 are preferably selected to have sensitivity to a broad range of wavelengths in the UV band, with both photodiodes having substantially similar peak sensitivity wavelengths. When the response of sample photodiode 193 is divided by the response of reference photodiode 195, the result is a value indicative of the relative reflectance of wafer 103 over wavelengths in the UV band, with the peak sensitivity wavelength having more weight in the measure of relative reflectance than other wavelengths. The measured relative reflectance value can be calibrated to generate a signal indicative of the true reflectance of the sample in the UV band.

To avoid the need to apply a complicated algorithm (assuming a weighted average of many incident wavelengths) to compute film thickness, processor 200 of the system determines a single effective wavelength for the broadband UV incident on each of photodiodes 193 and 195. The analog output of photodiodes 193 and 195 is digitized (and otherwise processed) in electronic circuitry 190 before undergoing digital processing in processor 200.

The optical subsystem shown in FIG. 13 may be further configured as described herein. For example, the dual channel optical subsystem may include one or more hollow optical fibers (not shown). The hollow optical fiber(s) may be configured as described above. In one embodiment, the dual channel optical subsystem may include a hollow optical fiber that transmits light from light source 110 to aperture mirror 128 or another optical component of the dual channel optical subsystem. The hollow optical fiber may also be configured such that a position of the light source may be substantially stationary during movement of other optical components of the dual channel optical subsystem, as described with respect to FIGS. 10 and 11. The system may be configured to move these other optical components of the dual channel optical subsystem with respect to the specimen to perform measurements at different locations on the specimen. Eliminating movement of the light source during scanning has advantages that are further described above.

In order to use this dual-beam spectrophotometer at VUV wavelengths (either on its own or in combination with other measurement systems), it is advantageous to enclose the optics in an inert atmosphere (except possibly the detectors and their associated optics) and use two differential apertures. The optical subsystem shown in FIG. 13 is preferably disposed within purged environment 208. The purged environment may be provided as described above. For instance, the purged environment may be created within housing 210 that surrounds a least a portion of the optical subsystem. In addition, a system that includes the optical subsystem shown in FIG. 13 may include a purging subsystem (not shown in FIG. 13) that is configured to maintain a purged environment around the dual channel optical subsystem during measurements by the optical subsystem. The purging subsystem may be a differential purging subsystem as described above. Housing 210 may also be configured as described above.

One or more components of the optical subsystem may be disposed outside of the housing in a non-purged environment. For example, as shown in FIG. 13, concave mirror 150 may be located outside of the housing in a non-purged environment. In addition, although detectors 172 and 174 are shown to be located inside of the housing in the purged environment, the detectors may alternatively be located outside of the housing in a non-purged environment. In addition, other components coupled to the optical subsystem are located outside of the housing and in a non-purged environment. These components include electronic circuitry 190 and processor 200. Placing components such as the detectors, electronic circuitry, and processor outside of the purged environment may reduce the area of the purged environment within the housing thereby reducing the cost and time of creating the purged environment.

Concave mirror 150 may be placed outside of the purged environment, not for space considerations, but to create optical conditions in the reference channel that are similar to those in the sample channel. For example, the dual-beam spectrophotometer has two light paths (sample and reference) which run parallel for most of their lengths. However, the reference channel cannot be reflected from the wafer. Unless a second differential aperture is added near reference mirror 150, the reference beam will not experience the same amount of absorption as the sample beam, which passes through a differential aperture within, or near, the objective. For example, housing 210 includes differential aperture 212 through which sample beam 146 is focused onto specimen 103 by objective 140. The differential aperture may be configured as described above. Outside of the differential aperture, sample beam 146 passes through a non-purged space. Therefore, the sample beam may be partially absorbed by unwanted molecules in this non-purged space. This absorption will alter the characteristics of the light that is measured by sample linear photodiode array 172.

If reference beam 148 is not similarly altered to account for absorption of the sample beam, the measurements of the dual beam spectrophotometer may be inaccurate. Therefore, the optical subsystem is configured such that at least a portion of the reference beam passes through a non-purged space. One embodiment shown in FIG. 13 includes positioning concave mirror 150 outside of housing 210. Housing 210 includes second differential aperture 214 through which reference beam 148 is directed onto concave mirror 150. Differential aperture 214 may be configured as described above.

Ideally, the reference aperture is at a substantially similar distance from the reference mirror surface as the objective aperture is from the wafer surface. For example, the concave mirror is spaced from differential aperture 214 by a distance that is approximately equal to the distance that specimen 103 is spaced from differential aperture 212. In this manner, the reference beam may pass through an amount of non-purged space that is approximately equal to the amount of non-purged space through which the sample beam passes. As such, the absorption of reference beam 148 and sample beam 146 may be approximately equal due to unwanted molecules in both non-purged spaces. In this manner, the purging subsystem is configured to maintain the same level of purging in both channels of the dual channel optical subsystem. Consequently, the light that is measured by sample linear photodiode array 172 and reference linear photodiode array 174 may be altered in substantially equal ways thereby increasing the accuracy of the measurements of the dual beam spectrophotometer.

Such "normalization" of the optical channels for absorption may be implemented if other components of the optical subsystem are disposed in the non-purged environment. For example, if detectors 172 and 174 are located outside of the purged environment, two separate differential apertures (not shown) may be formed in the housing to allow the reference and sample beams to by directed to the different detectors in a spatially separated manner. The space between the photosensitive elements of the detectors and the respective differential apertures may be approximately equal such that absorption of the reference and sample beams outside of the housing may be approximately equal.

In addition, many different optical subsystems known in the art have multiple channels such as a beam profile reflectometer and some optical subsystems designed particularly for inspection. Multiple channels of any such optical subsystem, which is disposed within a purged environment, may be "normalized" for absorption in a similar manner.

A system configured for measurement of a specimen that includes a dual channel optical subsystem may be further configured as described herein. For example, the dual channel optical subsystem may be included in a system that includes one or more additional optical subsystems. The one or more additional subsystems may be configured to perform additional measurements of the specimen using non-VUV light. The one or more additional optical subsystems may be disposed within a non-purged environment. For example, the dual channel optical subsystem may be included in the system illustrated in FIG. 1 as the first optical subsystem in place of the ellipsometer. Such a system may include a second optical subsystem that is configured as a reflectometer as described with respect to FIG. 1. Alternatively, the reflectometer may be replaced with a variety of other optical subsystems such as an ellipsometer (e.g., a single wavelength ellipsometer or a spectroscopic ellipsometer), a scatterometer, etc.

Figure 14:
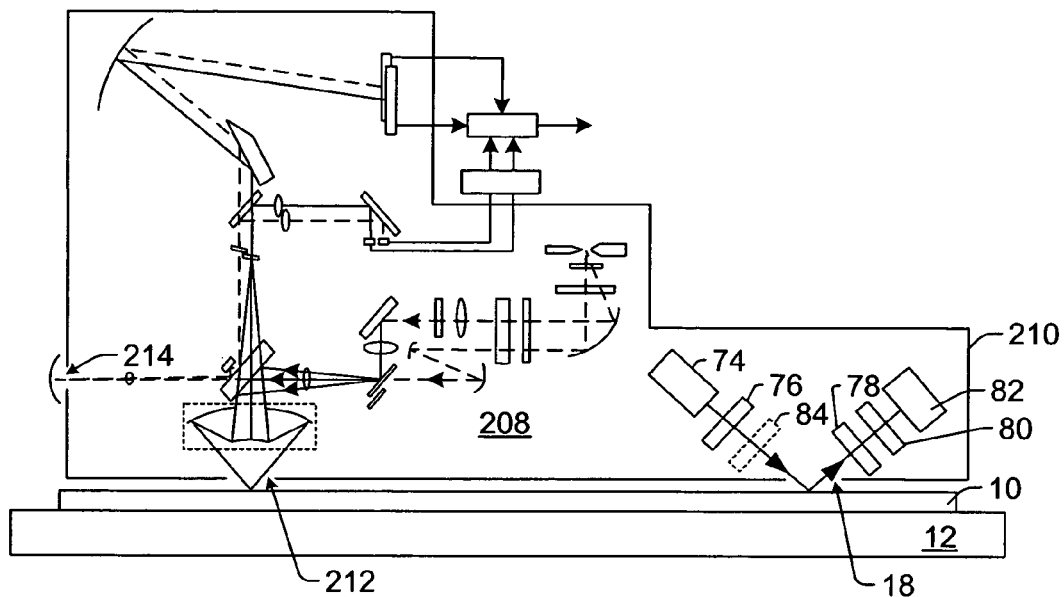
FIG. 14 is a schematic diagram illustrating a cross-sectional side view of the dual channel optical subsystem of FIG. 13 and an additional optical subsystem, both disposed within a purged environment.

In some embodiments, a system may include two or more optical subsystems disposed within a purged environment. For example, the system may include a dual channel optical subsystem such as that shown in FIG. 13 in addition to another optical subsystem, both disposed within a purged environment. One such embodiment is illustrated in FIG. 14. The reference numerals for components of the dual channel optical subsystem are not included in FIG. 14. However, all of the components of the dual channel optical subsystem shown in FIG. 14 are also illustrated in FIG. 13 along with corresponding reference numerals. Therefore, for details of the components of the dual channel optical subsystem illustrated in FIG. 14, one can refer to FIG. 13 and the corresponding description.

As shown in FIG. 14, the additional optical subsystem disposed within purged environment 208 along with the dual channel optical subsystem has the configuration of the first optical subsystem illustrated in FIG. 1. In particular, the additional optical subsystem in this embodiment is configured as an ellipsometer. The ellipsometer includes light source 74, polarizer 76, analyzer 78, and detector 82, all of which may be configured as described above. In addition, the ellipsometer may optionally include one or more filters 84 and spectrometer 80, both of which may also be configured as described above. In one embodiment, the additional optical subsystem may be configured as a single wavelength ellipsometer. The single wavelength ellipsometer may be configured to perform measurements of the specimen at a wavelength of 157 nm. In an alternative embodiment, the additional optical subsystem may be configured as a spectroscopic ellipsometer. In such an embodiment, light source 74 may be a VUV light flash lamp.

In other embodiments, the additional optical subsystem disposed in the same purged environment as the dual channel optical subsystem may have other configurations. For example, the additional optical subsystem may be configured as a reflectometer, a spectroscopic reflectometer, a scatterometer, a spectroscopic scatterometer, a different dual channel optical subsystem, or any other measurement subsystem known in the art. In further embodiments, more than one additional optical subsystem may be disposed in the same purged environment as the dual channel optical subsystem. For example, additional optical subsystems configured as an ellipsometer and a reflectometer may be disposed within the same purged environment as the dual channel optical subsystem. Alternatively, additional optical subsystems configured as an ellipsometer and a scatterometer may be disposed within the same purged environment as the dual channel optical subsystem.

As shown in FIG. 14, housing 210 has two differential apertures 212 and 214 for the dual channel optical subsystem. The sample beam directed to the specimen passes through differential aperture 212, and the reference beam directed to mirror 150 passes through differential aperture 214. As described further above, the two differential apertures and the purging subsystem (not shown in FIG. 14) are configured such that the same level of purging is maintained in both channels of the dual channel optical subsystem. In addition, housing 210 includes differential aperture 18 for the additional optical subsystem. The light directed to specimen 10 from the additional optical subsystem and returned from specimen 10 to the additional optical subsystem passes through this differential aperture. Therefore, the housing contains three differential apertures. In addition, if more than two optical subsystems are disposed within the purged environment within housing 210, the housing may have additional differential apertures for these additional optical subsystems.

Figure 15:
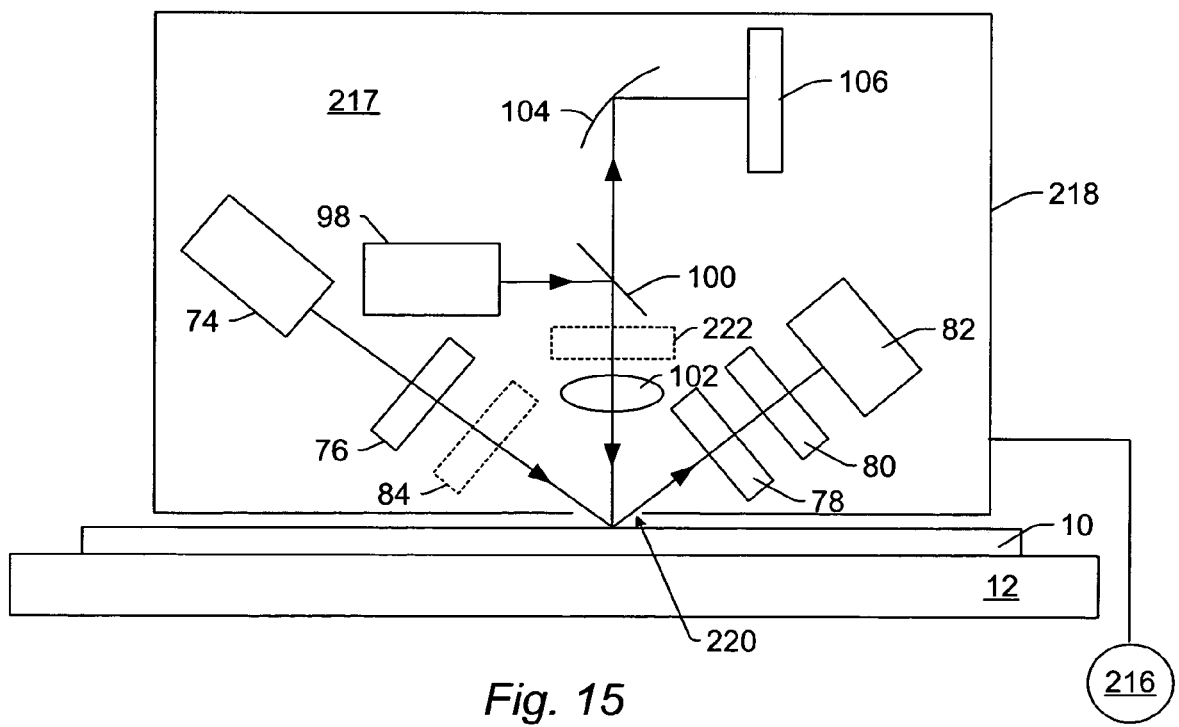
FIGS. 15 and 16 are schematic diagrams illustrating cross-sectional side views of different embodiments of two of more optical subsystems disposed within a purged environment.

FIG. 15 illustrates one embodiment of two optical subsystems that are configured to perform measurements of a specimen using VUV light. Although only two optical subsystems are illustrated in FIG. 15, it is to be understood that more than two optical subsystems may be included in such an embodiment. The two optical subsystems shown in FIG. 15 may be included in a system configured for measurement of a specimen. Such a system may be further configured as described herein.

The two optical subsystems are coupled to purging subsystem 216. Purging subsystem 216 is configured to maintain purged environment 217 around the two optical subsystems during measurements of specimen 10. The purging subsystem may be further configured as described above. For example, the purging subsystem may be a differential purging subsystem. In addition, the purging subsystem is configured to maintain approximately the same level of purging in the two optical subsystems. For example, the two optical subsystems may be disposed within housing 218. The housing may be configured as described above. In addition, the housing includes differential aperture 220, which is configured such that VUV light from the two optical subsystems can be directed to specimen 10 through the differential aperture and such that light returned from the specimen can pass through the differential aperture and be collected by the two optical subsystems. Differential aperture 220 may be further configured as described above.

One of the two optical subsystems in this embodiment is configured as an ellipsometer. The ellipsometer includes light source 74, polarizer 76, analyzer 78, and detector 82, all of which may be configured as described above. In addition, the ellipsometer may optionally include one or more filters 84 and spectrometer 80, both of which may also be configured as described above. In one embodiment, the optical subsystem may be configured as a single wavelength ellipsometer. The single wavelength ellipsometer may be configured to perform measurements of the specimen at a wavelength of 157 nm. In an alternative embodiment, the optical subsystem may be configured as a spectroscopic ellipsometer. In such an embodiment, light source 74 may be a VUV light flash lamp.

The other of the two optical subsystems in this embodiment is configured as a reflectometer, which may be configured as described above. For example, the second optical subsystem includes light source 98. Light source 98 may be a monochromatic or near monochromatic light source. In this embodiment, the reflectometer may be configured as a single wavelength reflectometer. In another embodiment, the light source may be a polychromatic light source or broadband light source. In such an embodiment, the reflectometer may be configured as a spectroscopic reflectometer. The second optical subsystem also includes beam splitter 100, lens 102, diffraction grating 104, and detector array 106, all of which may be configured as described above.

In some embodiments, therefore, the two optical subsystems shown in FIG. 15 may include an ellipsometer (e.g., a single wavelength ellipsometer or a broadband ellipsometer) and a reflectometer (e.g., a single wavelength reflectometer or a broadband spectroscopic reflectometer). In another embodiment, the two optical subsystems may include a broadband spectroscopic ellipsometer as described above and a broadband reflective spectrometer, which is described in more detail below.

As described further above, the optical subsystem that is configured as an ellipsometer may include one or more filters 84 if the ellipsometer is configured to perform measurements of the specimen using VUV light and non-VUV light. The one or more filters may be inserted in the optical path of the ellipsometer to prevent a substantial amount of the VUV light from reaching the specimen during measurements with non-VUV light. In this manner, the specimen may be protected from potential damage by prolonged exposure to the VUV light. In a similar manner, the optical subsystem that is configured as a reflectometer may also include one or more filters 222 if the reflectometer is configured to perform measurements of the specimen using VUV light and non-VUV light. One or more filters 222 may not be placed in the optical path of the reflectometer during measurements with VUV light, but may be inserted in the optical path of the reflectometer during measurements with non-VUV light. One or more filters 222 may be configured to prevent a substantial amount of the VUV light from reaching the specimen during measurements with the non-VUV light thereby preventing potential damage of the specimen by prolonged and unnecessary exposure to the VUV light.

The two optical subsystems are shown in FIG. 15 to direct and collect light through the same differential aperture. In this manner, the two optical subsystems may be configured to measure approximately the same measurement spot on the specimen either simultaneously or sequentially. Alternatively, the two optical subsystems may be configured to direct and collect light through different differential apertures (not shown). For example, the optical subsystems may be laterally spaced apart within housing 218, and each optical subsystem may be coupled to a different differential aperture. As such, the two optical subsystems may be configured to measure different measurement spots on the specimen simultaneously. In addition, the two optical subsystems may measure the same measurement spot on the specimen sequentially.

A system that includes two optical subsystems configured to measure a specimen using VUV light such as those shown in FIG. 15 may also include one or more additional optical subsystems (not shown). The additional optical subsystem(s) may be configured to perform additional measurements of the specimen using non-VUV light. Therefore, the additional optical subsystem(s) may be disposed within a non-purged environment. In some embodiments, a first portion of the additional optical subsystem(s) may be disposed within the purged environment, and a second portion of the additional optical subsystem(s) may be disposed within a non-purged environment. One such embodiment is described further below. In addition, the two optical subsystems and the additional optical subsystem(s) may have at least one common optical component. The common optical component(s) may include the first portion of the additional optical subsystem(s) that is disposed within the purged environment. An example of such an embodiment is described further below. In some embodiments, the additional optical subsystem(s) may include a beam profile ellipsometer, a beam profile reflectometer, a broadband reflective spectrometer, or a combination thereof. Such optical subsystems are described further below.

FIG. 16 illustrates another embodiment of two optical subsystems that are configured to perform measurements of a specimen using VUV light. The optical subsystems shown in FIG. 16 are described in more detail in U.S. Pat. No. 6,515,746 to Opsal et al., which is incorporated by reference as if fully set forth herein. Some of the non-essential details of the system presented in this patent have been omitted from the description corresponding to FIG. 16 presented herein. However, it is to be understood that the system illustrated in FIG. 16 may be further configured as described in this patent. In addition, it will be obvious upon reading the description of several embodiments provided herein that the system illustrated in FIG. 16 has been altered to dramatically improve upon the system described in U.S. Pat. No. 6,515,746 to Opsal et al. The alterations include, for example, altering the system to include VUV optical subsystems and disposing the VUV optical subsystems in a purged environment. Other changes will be evident upon reading the description of FIG. 16 provided herein.

Although only two VUV optical subsystems are illustrated in FIG. 16, it is to be understood that more than two VUV optical subsystems may be included in such an embodiment. The two VUV optical subsystems shown in FIG. 16 may be included in a system configured for measurement of a specimen. Such a system may be further configured as described herein.

One of the two VUV optical subsystems is configured as a broadband reflective spectrometer. The other VUV optical subsystem is configured as a broadband spectroscopic ellipsometer. Both VUV optical subsystems are disposed within purged environment 224. Purged environment 224 may be provided and maintained by purging subsystem 226, which may be configured as described above. For example, the purging subsystem may be coupled to housing 228, and in one embodiment may be a differential purging subsystem.

The housing may be configured as described above. In addition, the purging subsystem is configured to maintain approximately the same level of purging in both of the two VUV optical subsystems.

Broadband reflective spectrometer (BRS) 230 simultaneously probes specimen 10 with multiple wavelengths of VUV light. BRS 230 uses lens 232 and includes a broadband spectrometer 234 which can be of any type commonly known and used in the prior art. Lens 232 may be a transmissive optical component formed of a material such as calcium fluoride ($CaF_2$). Such a lens may be a spherical, microscope objective lens with a high numerical aperture (on the order of 0.90 NA) to create a large spread of angles of incidence with respect to the sample surface, and to create a spot size of about one micron in diameter. Alternatively, lens 232 may be a reflective optical component. Such a lens may have a lower numerical aperture (on the order of 0.4 NA) and may be capable of focusing light to a spot size of about 10–15 microns. Spectrometer 234 shown in FIG. 16 includes lens 236, aperture 238, dispersive element 240, and detector array 242. Lens 236 may be formed of $CaF_2$.

During operation, probe beam 244 from VUV light source 246 is collimated by lens 245, directed by mirror 243, and focused through differential aperture 233 and onto specimen 10 by lens 232. The VUV light source may include any of the light sources described above. Lens 245 may be formed of $CaF_2$. The differential aperture may be configured as described above. In some embodiments, BRS 230 may be configured to perform additional measurements of the specimen using non-VUV light. The non-VUV light may be provided by VUV light source 246. Alternatively, the non-VUV light may be provided by light source 283 or another light source (not shown). In such an embodiment, BRS may include one or more filters 231. Filter(s) 231 may be configured to prevent a substantial amount of the VUV light from reaching the specimen during the measurements with the non-VUV light. Therefore, the filter(s) may protect the specimen from unwanted exposure to the VUV light during non-VUV measurements. During measurements with the VUV light, filter(s) 231 may be moved out of the optical path of beam 244 manually, mechanically, or automatically. Although filter(s) 231 are shown to be located between mirror 248 and lens 232, it is to be understood that the filter(s) may be positioned at a variety of locations in the optical path of beam 244 between VUV light source 246 and lens 232.

Light reflected from the surface of the sample passes through differential aperture 233 and lens 232, and is directed by mirror 248 (through mirror 250) to spectrometer 234. Lens 236 focuses the probe beam through aperture 238, which defines a spot in the field of view on the specimen surface to analyze. Dispersive element 240, such as a diffraction grating, prism, or holographic plate, angularly disperses the beam as a function of wavelength to individual detector elements contained in detector array 242.

The different detector elements measure the optical intensities of different wavelengths of light contained in the probe beam, preferably simultaneously. Alternately, detector 242 can be a charge-coupled device ("CCD") camera or a photomultiplier with suitably dispersive or otherwise wavelength selective optics. It should be noted that a monochrometer could be used to measure the different wavelengths serially (one wavelength at a time) using a single detector element. Further, dispersive element 240 can also be configured to disperse the light as a function of wavelength in one direction, and as a function of the angle of incidence with respect to the specimen surface in an orthogonal direction, so that simultaneous measurements as a function of both wavelength and angle of incidence are possible. Processor 252 processes the intensity information measured by detector array 242.

Although all optical components of BRS 230 are shown in FIG. 16 to be located within the housing and in purged environment 224, it is to be understood that one or more components of the BRS can be located outside of the housing in the non-purged environment. For example, VUV light source 246 may be located outside of the housing in the non-purged environment. Light from the VUV light source may be directed through a differential aperture (not shown) formed in the housing to lens 245. This differential aperture may also be configured as described herein.

Broadband spectroscopic ellipsometer (BSE) 254 is also configured to perform measurements of the specimen using VUV light. BSE 254 includes polarizer 256, focusing mirror 258, collimating mirror 260, rotating compensator 262, and analyzer 264. In some embodiments, BSE 254 may be configured to perform additional measurements of the specimen using non-VUV light. The non-VUV light may be provided by VUV light source 246. Alternatively, the non-VUV light may be provided by light source 283 or another light source (not shown). In such an embodiment, BSE may include one or more filters 235. Filter(s) 235 may be configured to prevent a substantial amount of the VUV light from reaching the specimen during the measurements with the non-VUV light. Therefore, the filter(s) may protect the specimen from unwanted exposure to the VUV light during non-VUV measurements. During measurements with the VUV light, filter(s) 235 may be moved out of the optical path of beam 244 manually, mechanically, or automatically. Although filter(s) 235 are shown to be located between mirror 266 and polarizer 256, it is to be understood that the filter(s) may be positioned at a variety of locations in the optical path of beam 244 between VUV light source 246 and specimen 10.

In operation, mirror 266 directs at least part of probe beam 244 to polarizer 256, which creates a known polarization state for the probe beam, preferably a linear polarization. Mirror 258 focuses the beam through differential aperture 233 onto the specimen surface at an oblique angle, ideally on the order of 70 degrees to the normal of the specimen surface. Based upon well known ellipsometric principles, the reflected beam will generally have a mixed linear and circular polarization state after interacting with the specimen, based upon the composition and thickness of the specimen's film 268 and substrate 270.

The reflected beam passes through differential aperture 233 and is collimated by mirror 260, which directs the beam to rotating compensator 262. Compensator 262 introduces a relative phase delay δ (phase retardation) between a pair of mutually orthogonal polarized optical beam components. Compensator 262 is rotated at an angular velocity c about an axis substantially parallel to the propagation direction of the beam, preferably by electric motor 272. Analyzer 264, preferably another linear polarizer, mixes the polarization states incident on it. By measuring the light transmitted by analyzer 264, the polarization state of the reflected probe beam can be determined.

Mirror 250 directs the beam to spectrometer 234, which simultaneously measures the intensities of the different wavelengths of light in the reflected probe beam that pass through the compensator/analyzer combination. Processor 252 receives the output of detector 242, and processes the intensity information measured by detector 242 as a function of wavelength and as a function of the azimuth (rotational)

angle of the compensator 262 about its axis of rotation, to solve the ellipsometric values ψ and Δ as described in U.S. Pat. No. 5,877,859 to Aspnes et al., which is incorporated by reference as if fully set forth herein.

Although all optical components of BSE 254 are shown in FIG. 16 to be located within the housing and in purged environment 224, it is to be understood that one or more components of the BSE can be located outside of the housing in the non-purged environment. For example, VUV light source 246 may be located outside of the housing in the non-purged environment. Light from the VUV light source may be directed through a differential aperture (not shown) formed in the housing to lens 245. This differential aperture may also be configured as described herein.

A system that includes the broadband reflective spectrometer and broadband spectroscopic ellipsometer described above may also include additional optical subsystem(s) configured to perform additional measurements of the specimen using non-VUV light. For example, the system may include non-VUV optical subsystems configured as a beam profile ellipsometer, a beam profile reflectometer, another optical subsystem, or a combination thereof. The one or more additional optical subsystems may be disposed within a non-purged environment. For example, at least a portion of the additional optical subsystem(s) are disposed within a non-purged environment outside of housing 228.

Beam profile ellipsometry (BPE) is discussed in U.S. Pat. No. 5,181,080 to Fanton et al., which is incorporated by reference as if fully set forth herein. BPE 274 includes laser 283 that generates probe beam 284. Laser 283 may be a solid state laser diode from Toshiba Corp. which emits a linearly polarized 3 mW beam at 673 nm. BPE 274 also includes quarter wave plate 276, polarizer 278, lens 280, and quad detector 282. In operation, linearly polarized probe beam 284 is focused on specimen 10 by lens 232 through differential aperture 233. Light reflected from the sample surface passes up through differential aperture 233 and lens 232, through mirrors 248, 286, and 288, and is directed into BPE 274 by mirror 290.

The position of the rays within the reflected probe beam correspond to specific angles of incidence with respect to the specimen's surface. Quarter-wave plate 276 retards the phase of one of the polarization states of the beam by 90 degrees. Linear polarizer 278 causes the two polarization states of the beam to interfere with each other. For maximum signal, the axis of polarizer 278 should be oriented at an angle of 45 degrees with respect to the fast and slow axis of quarter-wave plate 276. Detector 282 is a quad-cell detector with four radially disposed quadrants that each intercept one quarter of the probe beam and generate a separate output signal proportional to the power of the portion of the probe beam striking that quadrant.

The output signals from each quadrant are sent to processor 252. By monitoring the change in the polarization state of the beam, ellipsometric information, such as ψ and Δ, can be determined. To determine this information, processor 252 takes the difference between the sums of the output signals of diametrically opposed quadrants, a value which varies linearly with film thickness for very thin films.

Beam profile reflectometry (BPR) is discussed in U.S. Pat. No. 4,999,014 to Gold et al., which is incorporated by reference as if fully set forth herein. BPR 292 includes laser 283, lens 294, beam splitter 296, and two linear detector arrays 298 and 300 to measure the reflectance of the sample. In operation, linearly polarized probe beam 284 is focused through differential aperture 233 onto specimen 10 by lens 232, with various rays within the beam striking the sample surface at a range of angles of incidence. Light reflected from the specimen surface passes up through differential aperture 233 and lens 232, through mirrors 248 and 286, and is directed into BPR 292 by mirror 288. The position of the rays within the reflected probe beam correspond to specific angles of incidence with respect to the specimen's surface. Lens 294 spatially spreads the beam two-dimensionally. Beam splitter 296 separates the S and P components of the beam, and detector arrays 298 and 300 are oriented orthogonal to each other to isolate information about S and P polarized light. The higher angles of incidence rays will fall closer to the opposed ends of the arrays. The output from each element in the diode arrays will correspond to different angles of incidence. Detectors arrays 298 and 300 measure the intensity across the reflected probe beam as a function of the angle of incidence with respect to the specimen surface. Processor 252 receives the output of detector arrays 298 and 300, and derives the thickness and refractive index of thin film layer 268 based on these angular dependent intensity measurements by utilizing various types of modeling algorithms. Optimization routines which use iterative processes such as least square fitting routines are typically employed.

The system shown in FIG. 16 may also include additional components such as detector/camera 302. Detector/camera 302 is positioned above mirror 290, and can be used to view reflected beams off of specimen 10 for alignment and focus purposes.

In order to calibrate BPE 274, BPR 292, BRS 230, and BSE 254, the system may include wavelength stable calibration reference ellipsometer 304 used in conjunction with a reference sample (not shown). For calibration purposes, the reference sample ideally consists of a thin oxide layer having a thickness, d, formed on a silicon substrate. However, in general the sample can be any appropriate substrate of known composition, including a bare silicon wafer, and silicon wafer substrates having one or more thin films thereon. The thickness d of the layer need not be known or be consistent between periodic calibrations.

Ellipsometer 304 includes light source 306, polarizer 308, lenses 310 and 312, rotating compensator 314, analyzer 316, and detector 318. Compensator 314 is rotated at an angular velocity ψ about an axis substantially parallel to the propagation direction of beam 320, preferably by electric motor 322. It should be noted that the compensator can be located either between the specimen and the analyzer (as shown in FIG. 16) or between the specimen and polarizer 308. It should also be noted that polarizer 308, lenses 310 and 312, compensator 314, and polarizer 316 are all optimized in their construction for the specific wavelength of light produced by light source 306, which maximizes the accuracy of ellipsometer.

Light source 306 produces a quasi-monochromatic probe beam 320 having a known stable wavelength and stable intensity. This can be done passively, where light source 306 generates a very stable output wavelength which does not vary over time (i.e., varies less than 1%). Examples of passively stable light sources are a helium-neon laser, or other gas discharge laser systems. Alternately, a non-passive system can be used where the light source includes a light generator (not shown) that produces light having a wavelength that is not precisely known or stable over time, and a monochrometer (not shown) that precisely measures the wavelength of light produced by the light generator. Examples of such light generators include laser diodes, or polychromatic light sources used in conjunction with a color filter such as a grating. In either case, the wavelength of beam 320, which is a known constant or measured by a monochrometer, is provided to processor 252 so that ellipsometer 304 can accurately calibrate the optical measurement devices in the system.

Operation of ellipsometer 304 during calibration is further described in U.S. Pat. No. 6,515,746. Briefly, beam 320 enters detector 318, which measures the intensity of the beam passing through the compensator/analyzer combination. Processor 252 processes the intensity information measured by detector 318 to determine the polarization state of the light after interacting with the analyzer, and therefore the ellipsometric parameters of the sample. This information processing includes measuring beam intensity as a function of the azimuth (rotational) angle of the compensator about its axis of rotation. This measurement of intensity as a function of compensator rotational angle is effectively a measurement of the intensity of beam 320 as a function of time, since the compensator angular velocity is usually known and a constant.

By knowing the composition of the reference sample, and by knowing the exact wavelength of light generated by light source 306, the optical properties of the reference sample such as film thickness d, refractive index and extinction coefficients, etc., can be determined by ellipsometer 304. Once the thickness d of the film has been determined by ellipsometer 304, then the same sample is probed by the other optical measurement devices BPE 274, BPR 292, BRS 230, and BSE 254 which measure various optical parameters of the sample. Processor 252 then calibrates the processing variables used to analyze the results from these optical measurement devices so that they produce accurate results. In the above described calibration techniques, all system variables affecting phase and intensity are determined and compensated for using the phase offset and reflectance normalizing factor discussed in U.S. Pat. No. 6,515,746, thus rendering the optical measurements made by these calibrated optical measurement devices absolute.

The above described calibration techniques are based largely upon calibration using the derived thickness d of the thin film. However, calibration using ellipsometer 304 can be based upon any of the optical properties of the reference sample that are measurable or determinable by ellipsometer 304 and/or are otherwise known, whether the sample has a single film thereof, has multiple films thereon, or even has no film thereon (bare sample).

As shown in FIG. 16, a first portion of the non-VUV optical subsystems may be disposed within the purged environment, and a second portion of the non-VUV optical subsystems may be disposed within a non-purged environment. For example, a first portion of BPE 274 is disposed outside of housing 228, and a second portion of BPE 274 is disposed within the housing. The first portion of BPE 274 that is disposed outside of housing 228 in the non-purged environment includes laser 283, mirror 288, mirror 290, quarter wave plate 276, polarizer 278, lens 280, and quad detector 282. The second portion of BPE 274 that is disposed inside of housing 228 in the purged environment includes mirrors 243, 266, 286, and 248, and lens 232. Housing 228 may include differential apertures (not shown) or relatively small sections of material (not shown) that are transparent to the non-VUV light such that the light can pass from components of BPE 274 outside of housing 228 to components inside of the housing and vice versa.

In addition, a first portion of BPR 292 is disposed outside of housing 228, and a second portion of BPR 292 is disposed within the housing. The first portion of BPR 292 that is disposed outside of housing 228 in the non-purged environment includes laser 283, mirror 288, lens 294, beam splitter 296, and linear detector arrays 298 and 300. The second portion of BPR 292 that is disposed inside of housing 228 within the purged environment includes mirrors 243, 266, 286, and 248, and lens 232. Housing 228 may include differential apertures (not shown) or relatively small sections of material (not shown) that are transparent to the non-VUV light such that the light can pass from components of BPR 292 outside of housing 228 to components inside of the housing and vice versa.

Furthermore, a first portion of ellipsometer 304 is disposed outside of housing 228, and a second portion of ellipsometer 304 is disposed within housing 228. The first portion of ellipsometer 304 that is disposed outside of the housing in the non-purged environment includes light source 306 and polarizer 308. The second portion of ellipsometer 304 that is disposed inside of the housing in the purged environment includes lenses 310 and 312, rotating compensator 314, analyzer 316, and detector 318. Housing 228 may include a differential aperture (not shown) or a relatively small section of material (not shown) that is transparent to the non-VUV light such that the light can pass from components of ellipsometer 304 outside of housing 228 to components inside of the housing.

In some embodiments, the VUV optical subsystems and the non-VUV optical subsystems may have at least one common optical component. The common optical component(s) generally will include optical component(s) included in the non-VUV optical subsystems that are disposed in the purged environment. For example, lens 232 is common to BPE 274, BPR 292, BRS 230, and BSE 254. In addition, lens 232 is disposed within housing 228 in purged environment 224. In a similar manner, mirrors 243, 266, 286, and 248 are common to BPE 274, BPR 292, BRS 230, and BSE 254 and are disposed within housing 228 in purged environment 224. Ellipsometer 304, as shown in FIG. 16, does not have any optical components that are common to the other optical subsystems. Such separation from the other optical subsystems may be appropriate since the ellipsometer is used to calibrate the other optical subsystems.

In another preferred embodiment, the use of measurement technology operating at VUV wavelengths is combined with a desorber to remove molecular contamination from the surface of a specimen prior to measurement. Molecules from the environment can adhere to the surface of the specimen. Typically, these molecules will interact more strongly with the short wavelength radiation in the VUV than with longer wavelengths and can cause misleading or inaccurate measurement results. In the preferred embodiment, these molecules are removed immediately prior to the measurement by a laser beam as described in U.S. patent application Ser. No. 10/056,271 entitled "Laser-Based Cleaning Device For Film Analysis Tool" filed on Jan. 23, 2002, by Janik et al., which is incorporated by reference as if fully set forth herein. In alternative embodiments, the specimen is cleaned by a hot plate or radiant heat prior to being loaded in the measurement system. Some examples of hot plates are illustrated in U.S. Pat. No. 6,261,853 to Howell et al., U.S. Pat. No. 6,519,045 to Kwon, and U.S. Pat. No. 6,624,393 to Howell et al., all of which are incorporated by reference as if fully set forth herein.

All of the embodiments of a system configured for measurement of a specimen described herein may include a cleaning subsystem. The cleaning subsystem may be configured to remove contaminants from the specimen prior to measurement. The system also includes an optical subsystem configured to perform measurements of the specimen using VUV light. The optical subsystem is disposed within a purged environment. In contrast, the cleaning subsystem is disposed within a non-purged environment.

Figure 17:
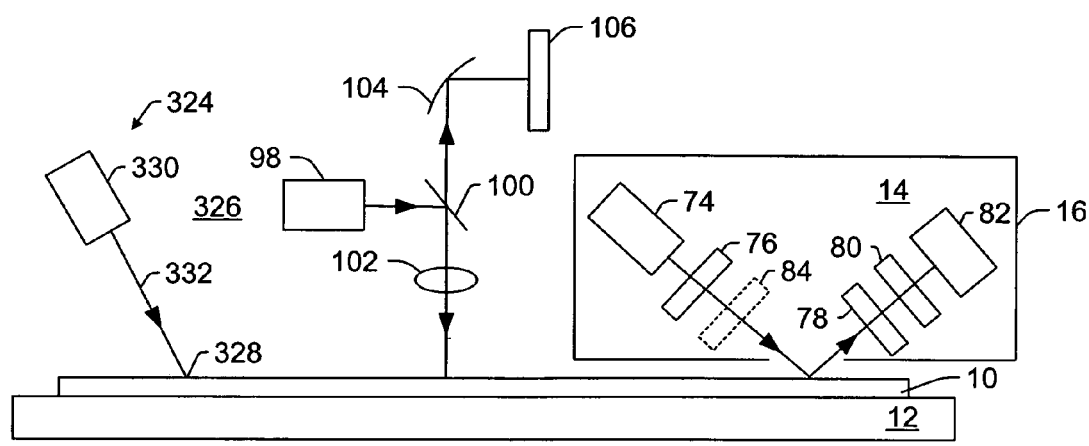
FIGS. 17 and 18 are schematic diagrams illustrating cross-sectional side views of different embodiments of a system configured for measurement of a specimen that includes a cleaning subsystem and an optical subsystem.

FIG. 17 illustrates one embodiment of a system configured for measurement of a specimen that includes a cleaning subsystem. This embodiment of the system is shown to include an optical subsystem that in this embodiment is configured as the first optical subsystem of FIG. 1, which is described in further detail above. However, the optical subsystem may include any optical subsystem described herein or known in the art. For example, the optical subsystem may be configured as an ellipsometer, a reflectometer, a scatterometer, a dual beam spectrophotometer, or a combination thereof. The optical subsystem is disposed within purged environment 14, which is created and maintained in housing 16 by a purging subsystem (not shown in FIG. 17). The purging subsystem may be configured as described above. For example, the purging subsystem may be a differential purging subsystem that is configured to provide the purged environment for the optical subsystem.

In some embodiments, the optical subsystem may also be configured to perform measurements of specimen 10 using VUV light as well as non-VUV light. For example, the optical subsystem may include one light source that is configured to provide both VUV light and non-VUV light. Alternatively, the optical subsystem may include two light sources, one configured to provide VUV light, and another configured to provide non-VUV light. Such light sources and configurations are described further above. In embodiments that the optical subsystem is configured to perform measurements using VUV light and non-VUV light, the optical subsystem may include one or more filters 84. The filter(s) may be configured to prevent a substantial amount of the VUV light from reaching the specimen during measurement with the non-UV light. The filter(s) may be further configured as described above.

The system may or may not also include an additional optical subsystem configured to perform additional measurements of specimen 10 using non-VUV light. For example, as shown in FIG. 17, the system may include an optical subsystem that is configured as the second optical subsystem of FIG. 1 which is generally configured as a reflectometer. However, the system illustrated in FIG. 17 may include optical subsystems other than reflectometers that are configured to measure the specimen using non-VUV light such as ellipsometers, scatterometers, dual beam spectrophotometers, a combination thereof and/or any other non-VUV optical subsystem known in the art. As shown in FIG. 17, the additional optical subsystem may be disposed within a non-purged environment outside of housing 16.

In an alternative embodiment, the system may include an additional optical subsystem (not shown in FIG. 17) that is configured to perform additional measurements of the specimen using VUV light. Such an additional optical subsystem may be disposed in purged environment 14. Embodiments that include more than one optical subsystem disposed in the same purged environment are illustrated in FIGS. 15 and 16, and the system illustrated in FIG. 17 may include such optical subsystems. In addition, it is to be noted that the number of optical subsystems that are disposed in one purged environment is not limited to two. In fact, it is conceivable that three, four, five, or any other number of optical subsystems may be disposed in the same purged environment. The optical subsystems may be further configured as described herein.

The system shown in FIG. 17 also includes cleaning subsystem 324 disposed in non-purged environment 326. For example, cleaning subsystem 324 is disposed outside of housing 16 and outside of purged environment 14 that is created and maintained within housing 16. As shown in FIG. 17, the cleaning subsystem and the optical subsystems are coupled to the same stage (i.e., stage 12). In this manner, the optical subsystem(s) may perform measurements on the specimen while the cleaning subsystem is removing contaminants from the specimen. Alternatively, the cleaning subsystem may be coupled to a different stage (not shown). The two stages may be coupled by a common specimen handler. Many specimen handlers such as wafer handlers are known in the art, and any specimen handler may be used as the common specimen handler. In such an embodiment, the optical subsystem(s) may perform measurements on one specimen while the cleaning subsystem is removing contaminants from a different specimen. In some such embodiments, the cleaning subsystem may be contained within a different module than the optical subsystem(s).

In the embodiment shown in FIG. 17, the cleaning subsystem includes a laser-based cleaning subsystem. Such a cleaning subsystem is configured to remove contaminants from localized area 328 on specimen 10. The cleaning subsystem is preferably configured to remove contaminants from a portion of the specimen prior to the measurements by the optical subsystem(s). Particularly, the cleaning subsystem is configured to remove contaminants from a portion of the specimen prior to measurements by VUV optical subsystem(s). Such a cleaning subsystem may be incorporated into all of the systems described herein.

One example of an appropriate laser-based cleaning subsystem is illustrated in U.S. patent application Ser. No. 10/056,271 entitled "Laser-Based Cleaning Device For Film Analysis Tool" filed on Jan. 23, 2002, by Janik et al., which is incorporated by reference as if fully set forth herein. As described in this patent application, cleaning subsystem 324 includes energy beam source 330. During the cleaning operation, a small portion of a contaminant layer (not shown) formed on the upper surface of specimen 10 is removed. The exposed portion (i.e., analysis area) of a layer (not shown) on the specimen is then analyzed during the measurement operation. The position of stage 12 can be shifted relative to energy beam source 330 and the optical subsystem(s) to enable cleaning and analysis at multiple locations on specimen 10.

To perform a cleaning operation, energy beam source 330 directs energy beam 332 at spot 328 on the contaminant layer. Energy beam 332 is configured to remove a portion of the contaminant layer by heating the contaminant layer directly or by heating the underlying portion of a layer on the specimen or the specimen. The portion of the contaminant layer heated in this manner is eventually vaporized, thereby exposing the underlying portion of a layer on the specimen or the specimen. This removal process can be aided by other mechanisms besides heating including the direct stimulation of the bonds between the contaminant layer and the specimen by photons from energy beam 332.

Because the heating from energy beam source 330 is confined to a localized area, the cleaning operation can be performed very rapidly, which minimizes any impact on analysis throughput. The potential for damage to the underlying layer and/or substrate is minimal because only a small portion of specimen 10 is heated. The risk of damage can be further reduced by performing the cleaning operation on non-functional regions of specimen 10 (e.g., regions such as scribe lines that will not be part of the functional portion(s) of the final devices to be made from specimen 10).

The amount of the contaminant layer to be removed depends on the measurement requirements of the optical subsystem(s). Modern thin film analysis tools generally require an analysis area of at least 20 µm×20 µm. Therefore, at least a 20 µm×20 µm portion of the contaminant layer would need to be removed for such systems. However, to ensure that the entire analysis area is uniformly cleaned, a larger portion of the contaminant layer could be removed.

According to an embodiment, energy beam source 330 could include a pulsed laser. For example, the contaminant layer could include a 5 angstrom thick layer of water and organic materials (which is similar to contamination layers often formed on modern thin film layers during production). A number of pulses or even a single pulse from a 5–100 µjoule laser having a 1–1000 ns pulse duration could then heat the desired portion of the contaminant layer to between roughly 300° C. to 1000° C., which is a temperature range sufficient to vaporize that portion of the contaminant layer. According to another embodiment, energy beam source 330 could include a Q-switched laser delivering a relatively high peak power, such as a frequency-doubled or tripled YAG (yttrium aluminum garnet) laser operating at wavelengths of 532 nm or 355 nm, respectively. According to another embodiment, other types of pulsed lasers operating at different wavelengths might be used including pulsed diode or alexandrite lasers. According to another embodiment, a continuous laser, such as an argon-ion laser, could be externally modulated (such as with an acousto-optic or electro-optic modulator) to produce a pulse. According to another embodiment, energy beam source 330 could including focusing optics (not shown) such as an optical fiber and a lens system configured to deliver a beam of the desired size and energy to spot 328 from a remote location (i.e., the optical fiber could transmit energy beam 332 from a remote beam generator to spot 328). According to another embodiment, energy beam source 330 could include a flash lamp coupled to focusing optics (not shown) to direct the high intensity light to the desired area on the contaminant layer.

Once the cleaning operation is complete, the measurement operation can be performed. Because specimen 10 does not need to be transferred to a different tool or process chamber, the measurement operation can be performed immediately following the cleaning operation so that the chance of recontamination of the exposed portion (analysis area) of the specimen is minimized. In this manner, a localized cleaning operation can be efficiently combined with a measurement operation to ensure accurate and repeatable analyses.

In the system shown in FIG. 17, energy beam source 330 and the optical subsystem(s) are not simultaneously focused at the same location on specimen 10. Consequently, an analysis operation performed using the optical subsystem(s) actually includes three steps: a cleaning operation, a positioning operation, and a measurement operation. During the cleaning operation, a small portion of the contaminant layer is removed by the energy beam from energy beam source 330. Then, during the positioning operation, specimen 10 is positioned such that light of one or more of the optical subsystems is aligned with the portion of the specimen exposed during the cleaning operation. The exposed portion of the specimen can then be analyzed by the optical subsystem(s) during the measurement operation.

In an alternative embodiment, energy beam 332 and a sample beam from one of the optical subsystems may be simultaneously directed at substantially the same location of specimen 10. For example, energy beam 332 and the light from the optical subsystem disposed in the non-purged environment may be simultaneously directed to substantially the same location on specimen 10. Therefore, the position of specimen 10 does not have to be adjusted between cleaning and measurement operations by this optical subsystem. Therefore, the measurement operation can be performed immediately after the cleaning operation to ensure that a new contaminant layer is not reformed over the analysis area. It is to be understood that the cleaning subsystem illustrated in FIG. 17 may be further configured as described in the above referenced patent application.

Figure 18:
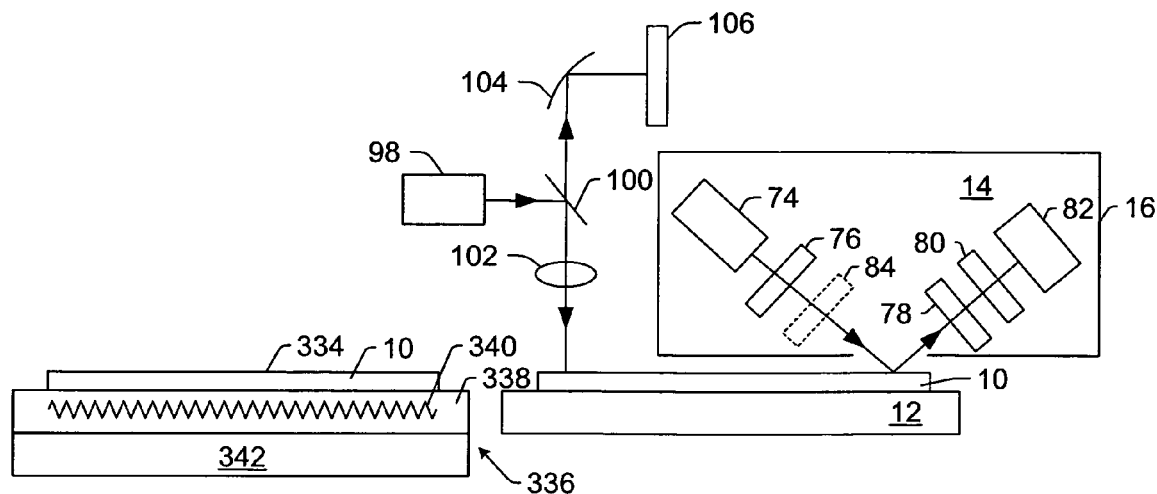

In a different embodiment shown in FIG. 18, the cleaning subsystem includes a heat-based cleaning subsystem. Such a cleaning subsystem is configured to remove contaminants from substantially an entire surface 334 of specimen 10. The cleaning subsystem is preferably configured to remove contaminants from a portion of the specimen prior to the measurements by the optical subsystem(s). Particularly, the cleaning subsystem is configured to remove contaminants from a portion of the specimen prior to measurements by VUV optical subsystem(s). Such a cleaning subsystem may be incorporated into all of the systems described herein.

The cleaning subsystem illustrated in FIG. 18 is a conventional wafer cleaning system 336 used to prepare specimen 10 for thin film analysis as described in U.S. Pat. No. 6,261,853 to Howell et al., U.S. Pat. No. 6,519,045 to Kwon, and U.S. Pat. No. 6,624,393 to Howell et al., which are incorporated by reference as if fully set forth herein. The cleaning subsystem performs a bulk heating operation to remove contaminants from a specimen. Specimen 10 may include a thin film layer (not shown) formed on a silicon substrate (not shown) and a contaminant layer (not shown) formed on the surface of the thin film layer. Cleaning subsystem 336 incorporates stage 338 that includes heating element 340. Heat generated by heating element 340 is conducted through stage 338 into specimen 10 thereby providing the heating required to vaporize the contaminant layer. Heat exchanger 342 coupled to stage 338 captures excess heat from heating element 340 thereby minimizing undesirable heating of the cleaning subsystem itself and the surrounding environment.

Stage 338 and stage 12 may be coupled by a common specimen handler (not shown). Many specimen handlers such as wafer handlers are known in the art, and any specimen handler may be used as the common specimen handler. After cleaning by cleaning subsystem 336, the specimen may be transferred to stage 12 by the common specimen handler. In such an embodiment, the optical subsystem(s) may perform measurements on one specimen while the cleaning subsystem is removing contaminants from a different specimen. In some such embodiments, the cleaning subsystem may be contained within a different module of the system than the optical subsystem(s).

In an alternative embodiment, the cleaning subsystem may be configured to heat the entire wafer in an oven (not shown) to a temperature of about 300° C. to vaporize any contaminants on the specimen. One example of a conventional oven-based wafer cleaning subsystem used to prepare a wafer for thin film analysis is described in U.S. Pat. No. 6,325,078 to Kamieniecki, which is incorporated by reference as if fully set forth herein. Such a cleaning subsystem may include multiple heating lamps (not shown), where thermal radiation from the heat lamps heats a specimen to vaporize contaminants on the specimen.

The systems shown in FIGS. 17 and 18 may include more than one cleaning subsystem. For example, a system may include a laser-based cleaning subsystem and a heat-based or oven-based cleaning subsystem. Both cleaning subsystems may be used to clean a specimen. The systems shown in FIGS. 17 and 18 may be further configured as described herein.

Current spectroscopic film measurement systems use a light source that has a substantially continuous spectrum, generally with a small number of peaks (e.g., 3 or less peaks) each riding on top of a substantially continuous background. The spectrum is detected by an array detector consisting of an array of pixels and the spectrum is spread out along the array. It is necessary to know the relationship between the pixel number and the wavelength in order to process the data into a film measurement. Wavelength calibration is performed occasionally with a separate light source that has a spectrum of a moderate number of widely separated peaks (e.g., 5 or less separated peaks). The pixel numbers on which these peaks lie are used to fit a function of pixel number versus wavelength. This function is used to process the data. One or more of the peaks in the measurement lamp spectrum can be used to update the wavelength calibration in the interval between calibration processes.

There are, however, some disadvantages to the above described measurement systems and methods. For example, the measurement spectrum can drift on the detector in the interval between calibration processes, and can even move during a measurement. These drifts and movements cause errors in the measurement because the relationship between wavelength and detector position is not what it is assumed to be. The peaks in the measurement source are difficult to track during a measurement or between measurement samples because the size and shape of the background changes during the measurement process for ellipsometers and changes between different samples for all spectral instruments. The imperfect peak tracking causes measurement errors. Also, if only a small number of peaks are used to track the spectrum, changes in the spectrum's scale (e.g., stretching or shrinking) cannot be completely accounted for.

Therefore, systems and methods have been developed for improving the accuracy and repeatability of a spectroscopic ellipsometer, polarimeter, reflectometer, or any other spectroscopic measurement system known in the art that is configured for measurement of a specimen. The system includes an optical subsystem that is configured to perform measurements of the specimen. In some embodiments, the measurements may include measurements of film properties. The optical subsystem may be configured as a spectroscopic ellipsometer, a polarimeter, a reflectometer, or any other spectroscopic measurement system described above or known in the art. Examples of ellipsometers and reflectometers are described above. In addition, examples of polarimeters are illustrated in U.S. Pat. No. 6,177,995 to Compain et al., U.S. Pat. No. 6,181,421 to Aspnes et al., U.S. Pat. No. 6,184,984 to Lee et al., U.S. Pat. No. 6,211,957 to Erdogan et al., U.S. Pat. No. 6,535,286 to Green et al., U.S. Pat. No. 6,591,024 to Westbrook, and U.S. Pat. No. 6,611,330 to Lee et al., all of which are incorporated by reference as if fully set forth herein. The optical subsystem may be further configured as described herein. For example, the optical subsystem may be disposed in a purged environment created by a purging subsystem. In another example, the optical subsystem may be included in a system with a non-VUV optical subsystem and/or a cleaning subsystem, which may be configured as described above.

In one embodiment, the optical subsystem includes a light source that is used for the measurements. The light source preferably generates light having a relatively large number of separated spectral peaks, with very little or substantially no continuous background. There are a large number of light sources that can be used to generate light having a relatively large number of separated spectral peaks, especially in the deep VUV, extreme ultraviolet (EUV), and soft x-ray regions of the spectrum. Therefore, the optical subsystem may include a light source that is configured to generate VUV light, EUV light, or soft x-rays. VUV light is defined above. EUV light is generally defined as light having wavelengths between about 100 nm and about 10 nm. Soft x-rays are generally defined as having wavelengths between about 10 nm and about 0.5 nm. In addition, the optical subsystem, in some embodiments, may include a light source that is configured to generate light having wavelengths of less than about 200 nm.

Figure 19:
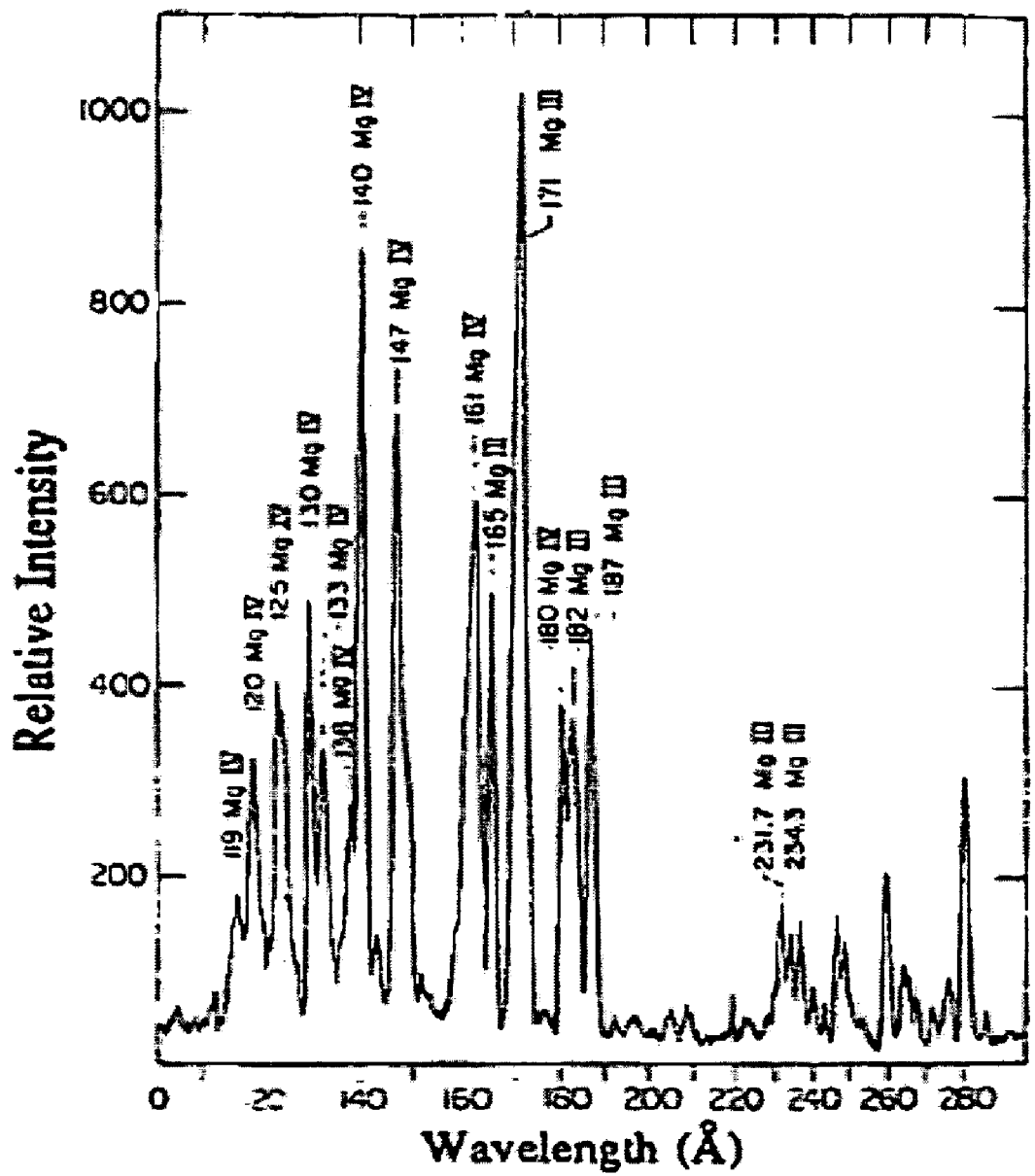
FIG. 19 is a plot illustrating a spectrum of a Penning discharge with a magnesium cathode and neon buffer gas.

In one example, Penning or hollow-cathode discharges with various metals or alloys of metal used in the cathodes can be included in the optical subsystem. A spectrum of a Penning discharge with a magnesium (Mg) cathode and neon (Ne) buffer gas is shown in FIG. 19. As shown in FIG. 19, which is taken from the book "Vacuum Ultraviolet Spectroscopy I", by James A. Sampson, p. 77, the spectrum of the Penning discharge includes 16 separated spectral peaks. However, the light source may provide a different number of separated spectral peaks. Preferably, the light source provides about 5 or more separated spectral peaks and more preferably about 10 or more separated spectral peaks. In another example, in the spectrum between about 160 nm and 90 nm, the spectrum of $H_2$ includes a relatively large number of narrow peaks. Discharges in mixtures of noble gases can also be used as the light source. High intensity pulsed laser harmonic generation and other non-linear processes can also be used to generate large numbers of sharp spectral peaks.

Examples of light sources that can be used to generate soft x-rays include a 1.064 μm neodymium YAG, laser which produces a xenon gas plasma that outputs soft x-ray radiation. Alternatively, another soft x-ray source may be used as the light source in the optical subsystem such as a synchrotron, discharge pumped x-ray lasers, an electron-beam driven radiation source device, or a radiation source based on high harmonic generation based on femto-second laser pulses. Other examples of light sources that can be used to generate soft x-rays are described in U.S. Pat. No. 6,522,717 to Murakami et al., which is incorporated by reference as if fully set forth herein. Any of the above-described light sources may be included in any of the optical subsystems described herein. The configuration of the optical subsystem may be altered depending on the selected light source. However, such design changes are well within the skill of one of ordinary skill in the art, and therefore will not be described further herein.

The optical subsystem also includes one or more detectors that are configured to detect light returned from the specimen. In some embodiments, the detector(s) may preferably be array detectors. There are several types of array detectors that can be used in the optical subsystem including, but not limited to, bare CCDs, photodiode arrays, microchannel plates (MCPs), and phosphor plates fiber-coupled to CCDs. Signals generated by the detector(s) may be processed by a processor and optionally one or more electronic components that may couple the detector to the processor. The processor may be further configured as described above. In addition, the processor may be coupled to the optical subsystem as described above.

When the measurement data is processed, the data may be processed by binning the signal into peaks. For example, a software algorithm can be used to partition the data into individual peaks. Peaks that span more than one pixel have their signal summed over the spanned pixels. The signal from each peak is considered to come from a single wavelength (e.g., the known wavelength of the peak center). In this way, the signal is processed using peaks as the fundamental unit of data, instead of pixels as in the current methods and systems.

The processor described above may perform these functions. For example, the processor may be configured to process data generated by the optical subsystem by partitioning the data into individual peaks spaced apart across a wavelength spectrum. The individual peaks correspond to the separated spectral peaks of the light generated by the light source. In addition, the processor may be configured to process data generated by the optical subsystem by summing signals for a peak in light detected by the optical subsystem if the peak spans more than one pixel on a detector of the optical subsystem. In a further example, the processor may be configured to process data generated by the optical subsystem by considering a signal from a peak in light detected by the optical subsystem as having a single wavelength. The single wavelength may include a known wavelength of a center of the peak. The processor may be further configured as described above.

In other embodiments, program instructions, which may be included in a carrier medium, that are executable on a computer system may be configured to perform the above described functions. For example, in one embodiment, the program instructions are executable on the computer system to analyze data generated by a detector of the optical subsystem by partitioning the data into individual peaks spaced apart across a wavelength spectrum. The individual peaks correspond to separate spectral peaks in light generated by the light source of the optical subsystem. In another embodiment, the program instructions are executable on the computer system to analyze the data by summing signals for one or more of the individual peaks if the individual peak(s) span more than one pixel on the detector. In a further embodiment, the program instructions are executable on the computer system to analyze the data by considering a signal from one or more of the individual peaks as having a single wavelength. The single wavelength includes a known wavelength of a center of the individual peak(s). The program instructions and the carrier medium may be further configured as described above. In addition, separate, different program instructions may be executable to perform the functions described above. The separate program instructions may or may not be included in one set of program instructions.

In one particular example, it may be desired to measure a substantially thin film. An EUV reflectometer containing a Penning discharge light source with a Mg cathode is used to collect reflectance data over a spectral range of about 12 nm to about 28 nm. The signal generated by the optical subsystem is binned into spectral peaks, and each peak is assigned its known central wavelength. The data may be further processed as described above.

The system and carrier medium embodiments described above have several advantages over the currently used systems and methods. For example, the wavelength calibration of the detector is automatically maintained at all times and is updated at each exposure of the detector. In addition, spectrum shift, drift, stretching, and shrinking are more completely accounted for than in the current methods and systems. Furthermore, the methods and systems described above would improve film measurement capability at substantially short wavelengths (e.g., less than about 200 nm). In particular, partitioning of the data as described above maintains a wavelength calibration of the detector, corrects for spectrum shift, drift, stretching, shrinking, or a combination thereof as the detector, and/or increases an accuracy of the measurements of the optical subsystem that are performed as a function of wavelength.

Further modifications and alternative embodiments of various aspects of the invention may be apparent to those skilled in the art in view of this description. For example, systems and methods for measurement of a specimen with vacuum ultraviolet light are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured for measurement of a specimen, comprising:
    an optical subsystem configured to perform measurements of the specimen using a light source configured to generate light having a relatively large number of separated spectral peaks with substantially no continuous background; and
    a processor configured to process measurement data generated by the optical subsystem using individual peaks in the measurement data as the fundamental unit of data, wherein the individual peaks correspond to the separated spectral peaks of the light generated by the light source.

2. The system of claim 1, wherein the light has wavelengths of less than about 200 nm.

3. The system of claim 1, wherein the light comprises vacuum ultraviolet light.

4. The system of claim 1, wherein the light comprises extreme ultraviolet light.

5. The system of claim 1, wherein the light comprises soft x-rays.

6. The system of claim 1, wherein the relatively large number of the separated spectral peaks comprises about 10 or more separated spectral peaks.

7. The system of claim 1, wherein the optical subsystem is further configured as a spectroscopic ellipsometer, a polarimeter, or a reflectometer, and wherein the measurements comprise measurements of thin film properties.

8. The system of claim 1, wherein the optical subsystem further comprises an array detector configured to detect light returned from the specimen.

9. The system of claim 1, wherein the processor is further configured to process the measurement data generated by the optical subsystem by considering a signal from a peak in light detected by the optical subsystem as having a single wavelength, and wherein the single wavelength comprises a known wavelength of a center of the peak.

10. The system of claim 1, wherein the processor is further configured to process the measurement data generated by the optical subsystem by summing signals for a peak in light detected by the optical subsystem if the peak spans more than one pixel on a detector of the optical subsystem.

11. The system of claim 1, wherein the processor is further configured to process the measurement data generated by the optical subsystem by partitioning the measurement data into the individual peaks spaced apart across a wavelength spectrum.

12. A carrier medium, comprising program instructions executable on a computer system to analyze measurement data generated by a detector of an optical subsystem by partitioning the data into individual peaks spaced apart across a wavelength spectrum and using the individual peaks as the fundamental unit of data, wherein the individual peaks correspond to a relatively large number of separated spectral peaks with substantially no continuous background in light generated by a light source of the optical subsystem, and wherein the optical subsystem is configured to perform measurements of a specimen using the light generated by the light source.

13. The carrier medium of claim 12, wherein the program instructions are further executable on the computer system to analyze the measurement data by summing signals for one or more of the individual peaks if the one or more of the individual peaks span more than one pixel on the detector.

14. The carrier medium of claim 12, wherein the program instructions are further executable on the computer system to analyze the measurement data by considering a signal from one or more of the individual peaks as having a single wavelength, and wherein the single wavelength comprises a known wavelength of a center of the one or more of the individual peaks.

15. The carrier medium of claim 12, wherein the partitioning of the measurement data maintains a wavelength calibration of the detector.

16. The carrier medium of claim 12, wherein the partitioning of the measurement data increases an accuracy of the measurements of the optical subsystem that are performed as a function of wavelength.

17. The carrier medium of claim 12, wherein the partitioning of the measurement data corrects for spectrum shift, drift, stretching, shrinking, or a combination thereof at the detector.

18. The carrier medium of claim 12, wherein the optical subsystem is further configured as a spectroscopic ellipsometer, a polarimeter, or a reflectometer, and wherein the measurements comprise measurements of thin film properties.

19. The carrier medium of claim 12, wherein the light has wavelengths of less than about 200 nm.

20. The carrier medium of claim 12, wherein the light comprises vacuum ultraviolet light.

21. The carrier medium of claim 12, wherein the light comprises extreme ultraviolet light.

22. The carrier medium of claim 12, wherein the light comprises soft x-rays.

* * * * *